United States Patent
Walstrom

(10) Patent No.: US 7,624,731 B2
(45) Date of Patent: Dec. 1, 2009

(54) HME/MDI APPARATUS HAVING MDI IN PARALLEL TO HME

(76) Inventor: Dennis R Walstrom, 251 W. Lake St., Excelsior, MN (US) 55331

( * ) Notice: Subject to any disclaimer, the term of this patent is extended or adjusted under 35 U.S.C. 154(b) by 455 days.

(21) Appl. No.: 11/374,722

(22) Filed: Mar. 14, 2006

(65) Prior Publication Data

US 2006/0219243 A1    Oct. 5, 2006

Related U.S. Application Data

(60) Provisional application No. 60/663,002, filed on Mar. 16, 2005.

(51) Int. Cl.
   *A62B 18/08* (2006.01)
(52) U.S. Cl. .............. 128/201.13; 128/204.17; 128/205.24
(58) Field of Classification Search ............ 128/201.13, 128/201.3, 203.16, 203.17, 203.26, 203.27, 128/204.17, 204.18, 204.21
   See application file for complete search history.

(56) References Cited

U.S. PATENT DOCUMENTS

| | | | |
|---|---|---|---|
| 4,819,834 A | 4/1989 | Thiel | |
| 5,178,138 A | 1/1993 | Walstrom et al. | |
| 5,261,538 A | 11/1993 | Evans et al. | |
| 5,477,992 A | 12/1995 | Jinks et al. | |
| 5,577,494 A | 11/1996 | Kuypers et al. | |
| 5,590,644 A | 1/1997 | Rosenkoetter | |
| 5,647,344 A | 7/1997 | Turnbull | |
| 5,938,085 A | 8/1999 | Conroy et al. | |
| 6,026,809 A | 2/2000 | Abrams et al. | |
| 6,089,227 A | 7/2000 | Nilsson | |
| 6,550,476 B1 * | 4/2003 | Ryder .................. | 128/201.13 |
| 6,588,421 B1 * | 7/2003 | Diehl et al. ........... | 128/201.13 |
| 6,626,171 B2 | 9/2003 | Sexton et al. | |
| 6,640,805 B2 | 11/2003 | Castro et al. | |
| 6,792,946 B1 | 9/2004 | Waldo, Jr. et al. | |
| 7,069,928 B1 * | 7/2006 | Waldo et al. ......... | 128/201.13 |
| 7,347,203 B2 * | 3/2008 | Marler et al. ......... | 128/201.13 |
| 2004/0123974 A1 | 7/2004 | Marler et al. | |
| 2006/0157056 A1 | 7/2006 | Burk | |

OTHER PUBLICATIONS

Richard D. Branson, Humidification for Patients with Artificial Airways, Respiratory Care, Jun. 1999, vol. 44, No. 6, Daedalus Enterprises Inc, Irving, Texas.

* cited by examiner

*Primary Examiner*—Justine R Yu
*Assistant Examiner*—Christopher Blizzard

(57) ABSTRACT

The present apparatus includes a metered dose inhaler (MDI) portion housed with a heat and moisture exchanger (HME) portion. The MDI portion and the HME portion share an inlet. The MDI portion and the HME portion share an outlet. The MDI portion and the HME portion are in parallel to each other and are immediately lateral of one another. The present MDI/HME apparatus includes a valve to direct fluid flow to or away from the HME portion and to or away from the MDI portion. The present MDI/HME apparatus includes a valve arm to communicate to the caregiver whether fluid is passing through the MDI portion or the HME portion and to structurally close off an MDI port when the valve is open relative to the HME portion. The valve is structured such that fluid flow to the patient is never obstructed.

17 Claims, 20 Drawing Sheets

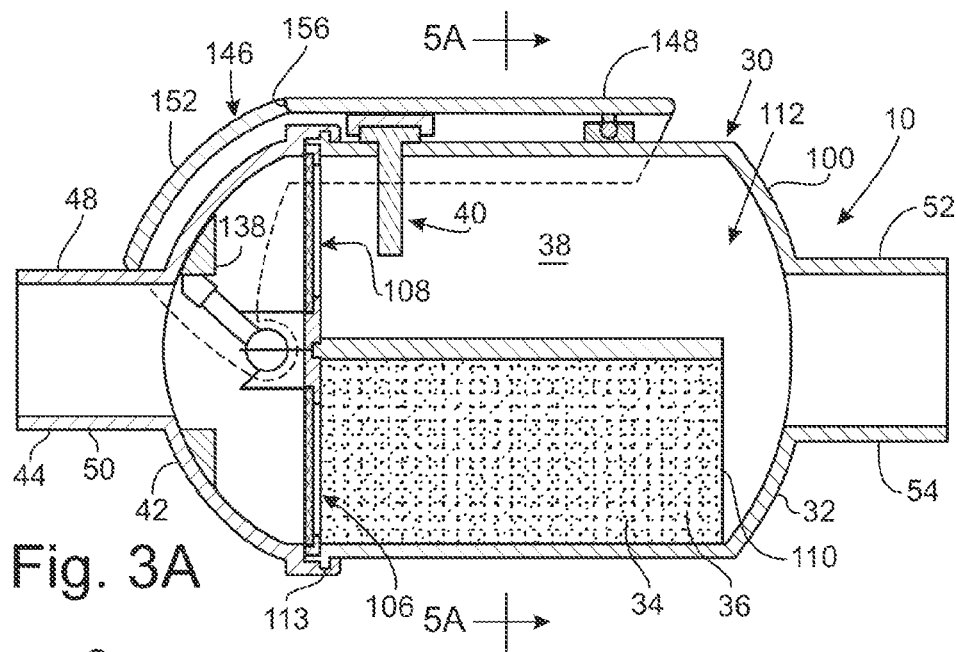
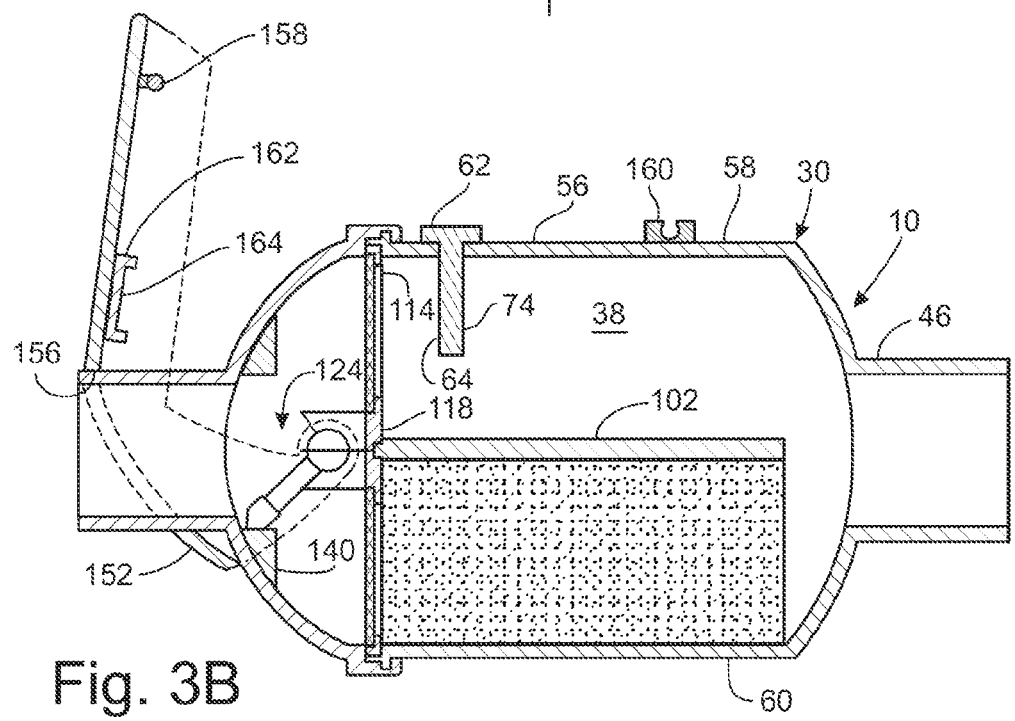

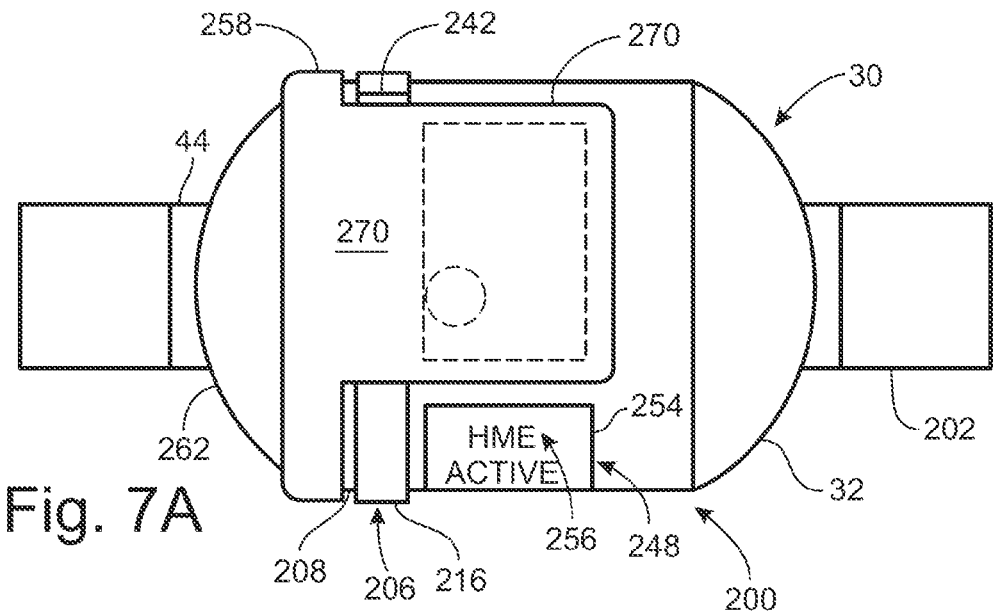
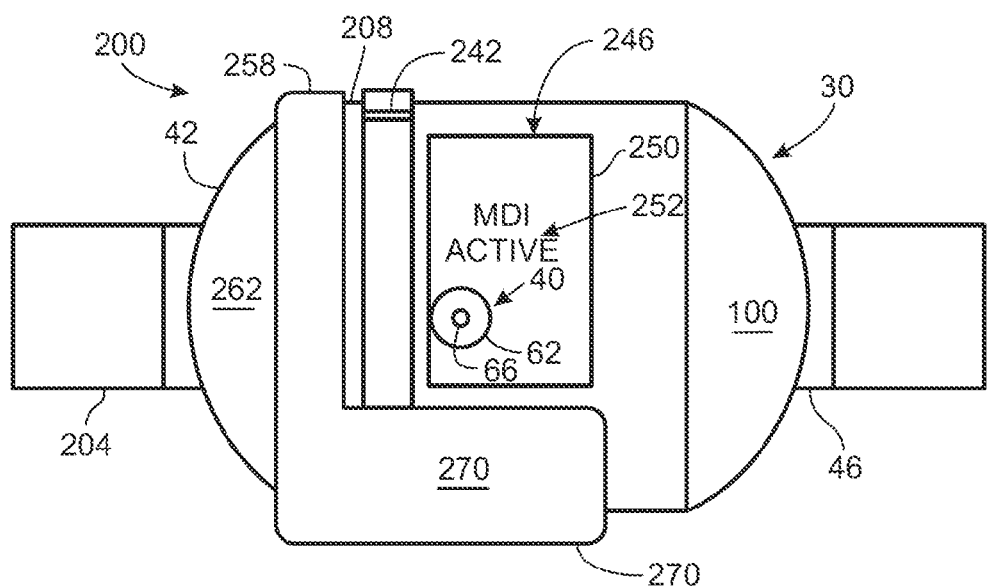

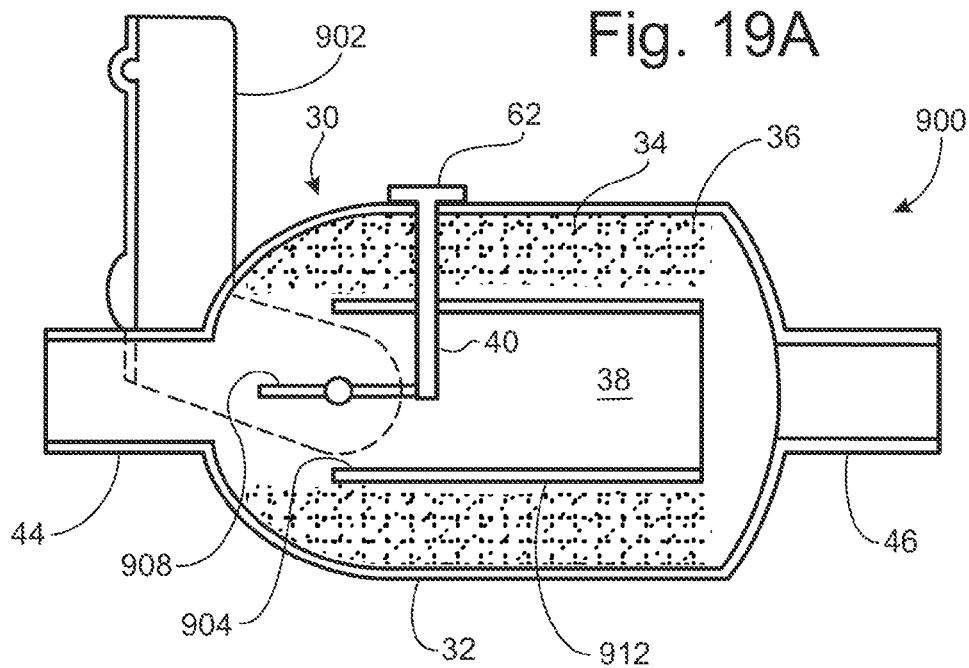
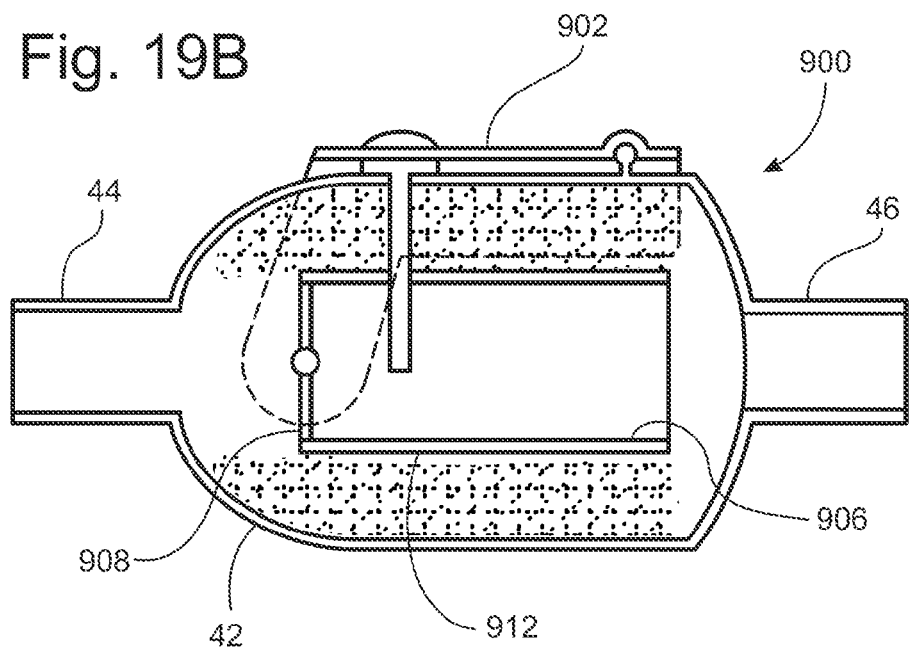

HME/MDI APPARATUS HAVING MDI IN PARALLEL TO HME

This application claims the benefit under 35 U.S.C. 119(e) of U.S. Provisional Patent Application No. 60/663,002 filed Mar. 16, 2005, which is hereby incorporated by reference in its entirety into this application.

FIELD OF THE INVENTION

The present invention relates generally to metered dose inhalers (MDIs) and heat and moisture exchangers (HMEs), particularly to the unique combination of an apparatus having each of a metered dose receiving chamber and heat and moisture exchanger, and specifically to an apparatus having a metered dose receiving chamber disposed in parallel to and laterally of a heat and moisture exchanger and sharing the same inlet and outlet that are engaged in a circuit of a mechanical ventilator.

BACKGROUND OF THE INVENTION

Metered dose inhalers (MDIs) were developed in the 1950s for treatment of certain respiratory conditions such as asthma, emphysema, bronchitis, and the like. MDIs have since become extremely popular for inpatient and outpatient treatment, due to their effectiveness, low comparative cost, portability, and ease of use. Their development has included the introductions of many different drugs and many different devices in which to use them. In the last fifteen years, MDIs have increasingly been used for mechanically ventilated patients, as opposed to the previous method of using compressed gas powered nebulizers to deliver aerosolized medications. Nebulizers are problematic due to the complexity and cost of associated equipment, difficult infection control, and labor costs.

An MDI is a small, pressurized canister containing multiple doses of medication in liquid form, a propellant, and other inert ingredients to stabilize the medication and prepare it for aerosolization. The canister also contains a metering valve, which precisely "meters" doses of medication prior to discharge. A spring loaded plunger discharges the measured dose of medication through an integral nozzle at the end of the canister, the medication then exiting the nozzle in a plume of very small particles. This plume is then actively inhaled by the patient, either through a MDI holder, an independently manufactured holding chamber or spacing device, or other mouthpiece. In the case of the mechanically ventilated patient, the MDI is discharged into an adapter in the inspiratory tubing of the ventilator or into a spacer placed in the inspiratory tubing of the ventilator. The ventilator cycled volume then carries the plume to the lungs of the patient under pressure via an artificial airway such as an endotracheal tube or tracheostomy tube. Some spacers or holding devices can be used interchangeably between intubated and non-intubated patients.

Heat and moisture exchangers (HME) are apparatus which passively collect heat and humidity exhaled by an intubated patient and passively return some of such heat and moisture to the patient in the subsequent breath. Since lungs and their conducting airways are reliant on moisture for their function, the lack of moisture for even a short period of time, such as a few hours, can be damaging to lung and airway tissues and can be potentially fatal. In the non-intubated patient, heat and moisture are supplied by the upper airway, including the nose, mouth, and oropharynx. The intubated patient has an endotracheal tube or tracheostomy tube passing through the upper airways, removing the patient's ability to add heat and moisture to incoming air. Air/oxygen mixtures delivered from mechanical ventilators are cold and virtually dry; conditioning the gas mixture with heat and moisture minimizes the loss of body heat and moisture through ventilation. An HME is a rigid walled apparatus with an inlet and an outlet connectable between a ventilator circuit and a tracheal tube or endotracheal tube and containing a medium which absorbs heat and moisture from a gas saturated with heat and moisture, such as gas exhaled by a patient; this medium releases heat and moisture to cooler and drier gas such as that being delivered by a mechanical ventilator. Some HMEs are referred to as hygroscopic condenser humidifiers (HCH). HCH use a chemically treated medium to absorb and release heat and moisture. In the scope of the present invention, a HCH is a form of an HME. The medium in an HME can be a simple sponge-like material, a chemically treated sponge-like material, a chemically treated paper or polypropylene material, or other such heat and moisture absorbing material. It also may contain metal or metallic fibers to increase heat exchanging properties. A great variety of heat and moisture exchanging media, or referred to interchangeably as HME medium, exists.

An HME is referred to as an HMEF with the addition of a filter, such that gas delivered by a ventilator is first passed through a filter medium integral in the HME.

An HME is placed between the distal end of a ventilator circuit and the proximal end of an endotracheal or tracheostomy tube; thus exhaled gas is partially re-breathed by the patient, and, along with the re-breathed gas and dry, incoming gas from a ventilator, some of the heat and moisture the patient previously exhaled.

In many institutions, HME are used for the first twenty-four hours or more of mechanical ventilation before switching to a conventional active heat and humidity system. The advantages of HME are that they require no complex humidity and heat generators, are low cost, and are effective in returning exhaled heat and moisture to the patient. For most patients using short term mechanical ventilation, HMEs are a cost effective alternative to expensive, electrically powered heat and moisture systems.

A heated humidifier (HH) is an active system for adding heat and moisture to ventilator circuits for intubated and non-intubated patients. An HH is typically mounted on a mechanical ventilator and is electrically powered. Gas exiting from the ventilator is passed through a HH chamber comprised of heated canister with or without an integral wick to increase efficiency. An HH can regulate the amount of moisture in the fluid in a mechanical ventilating circuit and can further regulate the temperature of the fluid passing through a mechanical ventilator circuit. HHs are bulky and are heated, such as electrically, and thus are not referred to as passive heat and moisture exchangers (HME).

MDI and nebulized medications cannot pass through HMEs, since the medium will block nearly all of the aerosol particles before they can be delivered to the airway. This will also eventually clog the HME. To avoid this, current practice requires that the HME be removed from the circuit and substituted with an MDI spacer or conduit adapter. After medication is delivered via the MDI spacer, the spacer or conduit is removed and the HME is replaced. This procedure may occur as often as every hour or two, or at longer periods such as every 12 hours or so. Each time the circuit is opened for this procedure, there is risk of biocontamination of the circuit, and thus, the patient's airways. This is documented to be a cause of ventilator associated pneumonia (VAP). Another potential problem with opening ventilator circuits is the loss of end-expiratory pressure, resulting in collapse of lung segments. In certain disease states, it is very difficult to re-inflate these segments; the result is loss of ventilated lung tissue and altered gas exchange; this can be life threatening.

SUMMARY OF THE INVENTION

The present invention includes a combined HME/MDI apparatus, containing a MDI section with an integral MDI nozzle, and a HME, separated in one housing, with an active valve, allowing the user to select whether the MDI or HME section is used to either deliver metered dose medications or heat and moisture to the intubated mechanically ventilated patient. In addition, the MDI section can be used as a conduit to deliver aerosolized medications from other sources in the inspiratory limb of a ventilator circuit and external from the described apparatus.

The combined HME/MDI apparatus is placed between the wye outlet of the ventilator circuit and the endotracheal or tracheostomy tube. During regular or normal ventilation, which requires heat and humidity, the HME section is open to flow through HME medium during both inspiration and expiration. During exhalation, the HME medium absorbs some of the heat and moisture exhaled by the patient. During the subsequent inspiration, some of the heat and moisture retained in the HME medium is absorbed by the cold and dry gas or fluid delivered to the patient by the ventilator. In this way, the airways and lungs of the patient are adequately warmed and moistened.

When a MDI medication must be delivered to the lungs of the patient, the practitioner switches a valve to redirect the fluid flow from the ventilator to the MDI section instead of the HME section, and attaches a MDI canister to the nozzle inlet of the MDI section. The medication is discharged into the MDI section and delivered to the patient during an inspiration from the ventilator, and is repeated as many times as are prescribed. When the MDI medication delivery is completed, the MDI canister is removed from the nozzle, and the valve is switched to direct fluid flow back through the HME section, again providing heat and moisture to the patient.

A feature of the present invention is the provision, in an HME/MDI apparatus having a housing with an inlet and outlet for being engaged in a circuit of a mechanical ventilator, of a first interior section of the housing having an HME and of a second interior section of the housing being in fluid communication with a port for an MDI.

Another feature of the present invention is the provision in such an HME/MDI apparatus, of the first (HME) interior section being disposed in parallel to the second (MDI) interior section.

Another feature of the present invention is the provision in such an HME/MDI apparatus, of the first (HME) interior section being lateral to the second (MDI) interior section.

Another feature of the present invention is the provision in such an HME/MDI apparatus, of the first (HME) interior section, or portion thereof, being immediately lateral to the second (MDI) interior section, or portion thereof.

Another feature of the present invention is the provision in such an HME/MDI apparatus, of a valve in the housing and confronting the inlet, with the valve selectively conveying fluid into the first and second interior sections.

Another feature of the present invention is the provision in such an HME/MDI apparatus, of a valve in the housing and confronting the inlet, with the valve selectively conveying fluid into the first and second interior sections, and with the valve having an arm extending out of the housing to communicate to a caregiver whether fluid is being directed to the first (HME) interior section or the second (MDI) interior section.

Another feature of the present invention is the provision in such an HME/MDI apparatus, of a valve in the housing and confronting the inlet, with the valve selectively conveying fluid into the first and second interior sections, with the valve having an arm extending out of the housing to communicate to a caregiver whether fluid is being directed to the first (HME) interior section or the second (MDI) interior section, with a portion of the arm confronting and closing off an MDI seat on the housing when the valve is positioned to direct fluid to the first (HME) interior section, and with the arm being out-of-the-way of the MDI when the valve is positioned to direct fluid to the second (MDI) interior section.

Another feature of the invention is the provision in an HME/MDI apparatus, of a housing comprising an inlet, an outlet, an HME section, and an MDI section, with the HME section and MDI section being disposed in parallel in the housing, of HME media in the HME section, of an MDI port on the housing and leading to the MDI section, of a valve in the housing and selectively conveying fluid from the mechanical ventilator into one of the HME section and MDI section, and of an arm comprising an arm portion disposed outside of and confrontable with the housing, with the arm being engaged to the valve such that movement of the arm portion moves the valve and such that movement of the valve moves the arm portion, with said arm portion having a first position that renders the MDI port inoperable, with said arm portion having a second position that permits operation of the MDI port, with said first and second positions dependent upon a position of said valve.

Another feature of the present invention is the provision in an HME/MDI apparatus, of a valve structured such that fluid flow is available at all times from the inlet to the outlet and from the outlet to the inlet such that fluid flow to the patient is never cut off.

Another feature of the present invention is the provision, in an HME/MDI apparatus having a housing with an inlet and outlet for being engaged in a circuit of a mechanical ventilator, of a first interior section of the housing having an HME and of a second interior section of the housing being in fluid communication with a port for an MDI, of the housing being a singular housing, and of the housing being generally integral and one-piece.

A first advantage of the present invention relates to health and safety. This advantage is that risk of biocontamination is minimized because the substitution of an MDI spacer for an HME is eliminated, thereby keeping the ventilating circuit closed to outside contamination.

A second advantage of the present invention relates to health and safety. This advantage is a maintenance of end-expiratory pressure because risk of pressure loss is eliminated with the elimination of the repeated steps of substituting an HME for an MDI spacer and back again.

A third advantage of the present invention relates to health and safety. This advantage is a lessening of overall resistance to expiratory (or inspiratory) fluid flow in the mechanical ventilating circuit. As fluid flows through a circuit or a portion of a circuit, the flow of fluid slows as objects or apparatus are encountered. When a relatively great number of objects are encountered, resistance to fluid flow is relatively high. When a relatively few number of objects are encountered, resistance to fluid flow is relatively low. More objects necessarily lead to greater resistance. Less objects necessarily lead to a lesser resistance. Greater resistance and the attendant slow flow of fluid is undesirable because such can lead to 1) a greater work load on the diaphragm of the patient, 2) air-trapping or fluid-trapping and auto-positive end-expiratory pressure, and 3) media in the HME (or artificial nose) can accumulate secretions, blood or water, which can then clog the media, offering absolute resistance. Accordingly, greater resistance is offered to the two object longitudinally disposed combination of 1) an HME with simply a bypass and 2) an MDI upstream or downstream from the HME having the bypass. Lesser resistance is therefore offered by the present invention, an HME having a laterally opposed MDI, because only one object, the laterally opposed MDI or the laterally opposed HME, is encountered at one time by fluid being conveyed in the mechanical ventilating circuit.

A fourth advantage of the present invention relates to health and safety. This advantage is a closing off of the MDI seat on the housing when the valve is positioned to direct fluid to the first (HME) interior section. If particulate medication could be delivered to the second (MDI) interior section when the valve is directing fluid to the first (HME) interior section, the second (MDI) interior section would have no fluid flow therein, and such medication would not travel to the lungs of the patient being ventilated.

A fifth advantage of the present invention relates to health and safety. This advantage is a visual reminder when the arm operating the valve is raised to direct fluid flow into the MDI section. The raised or rotated arm reminds the practitioner that no humidity or heat is being exchanged. This helps to assure that the practitioner will be attentive to lowering or rotating back the arm, restoring passive humidity and heat exchange.

A sixth advantage of the present invention relates to health and safety. This advantage assures that flow is never decreased (or a decrease in flow is minimized) through the device because of inadvertent mis-positioning of the valve. Any position of the valve results in flow through one section proportional to flow in the opposing section. In other words, if the valve is open 50% to the MDI section, flow is also 50% through the HME section. If the flow is only 40% open to the MDI section, flow is 60% through the HME section, and so on. There is never any danger (or such danger is minimized) that flow is decreased or absent due to the position of the valve.

Another advantage of the present invention is cost. The cost of the present unique combination of an HME/MDI apparatus is less than the total cost of a stand alone HME and a stand alone MDI spacer. Further, the present HME/MDI apparatus is easy and inexpensive to manufacture.

BRIEF DESCRIPTION OF THE DRAWINGS

FIG. 3A is a sectional view of the HME/MDI apparatus of FIG. 2A showing the HME passage open, the MDI passage closed, and the MDI port blocked and sealed.

FIG. 3B is a section view of the HME/MDI apparatus of FIG. 3A showing the HME passage closed, the MDI passage open, and the MDI port accessible.

FIG. 7A is top plan view of an alternate embodiment of the HME/MDI apparatus showing an arm blocking off the MDI port.

FIG. 7B is a top plan view of the HME/MDI apparatus of FIG. 7A showing the arm rotated out of the way such that the MDI port is accessible.

FIG. 19A is a longitudinal section view of an alternate embodiment of the present HME/MDI apparatus, showing a butterfly valve permitting flow into each of the MDI and HME sections, which flow takes the course of least resistance into the MDI section.

FIG. 19B is a longitudinal section view of the embodiment of FIG. 19A showing the butterfly valve closing off the MDI section and directing flow to the HME section.

Figure 20A:
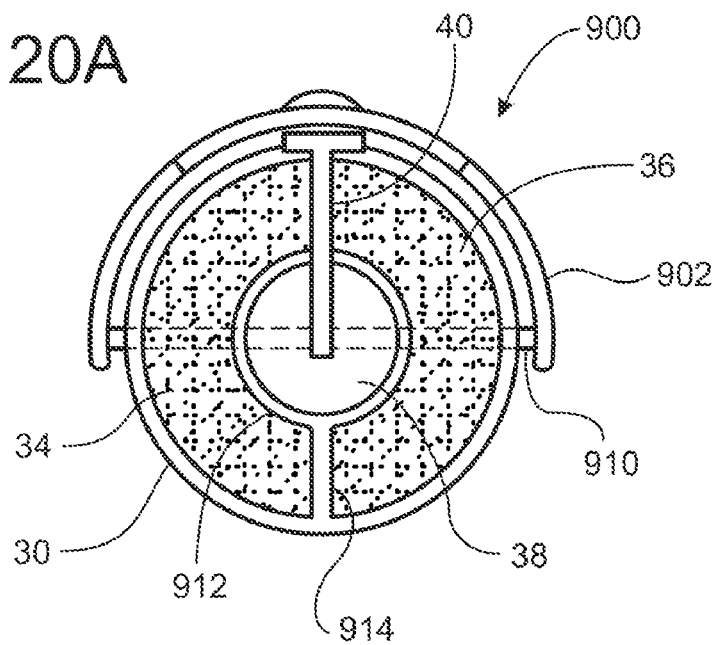

FIG. 20A is a lateral section view of the embodiment of FIG. 19A showing, among other features, how the MDI section is supported in the interior of HME section and how the exterior arm is engaged to the interior butterfly valve.

Figure 20B:
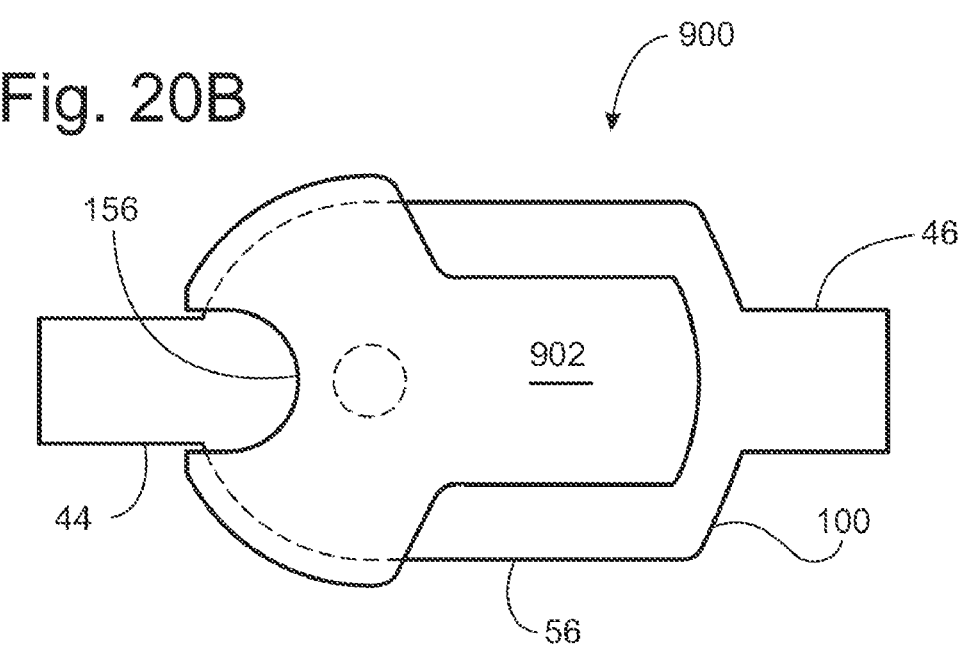

FIG. 20B is a top view of the embodiment of FIG. 19A and shows the exterior arm in a closed position.

DESCRIPTION

Figure 16:
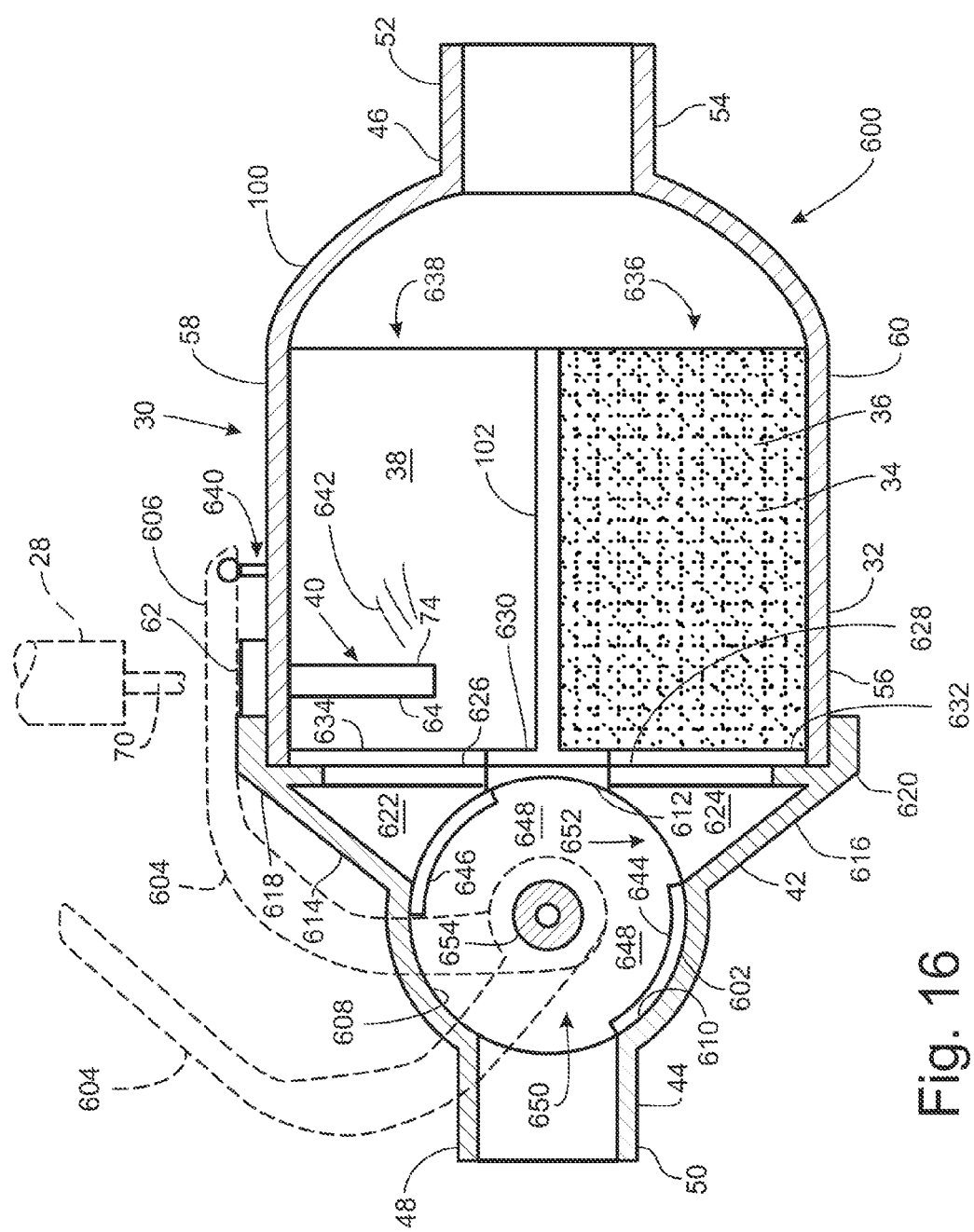
FIG. 16 is a side, generally sectional, and partially phantom view of an alternate embodiment of the present HME/MDI apparatus.
Figure 17:
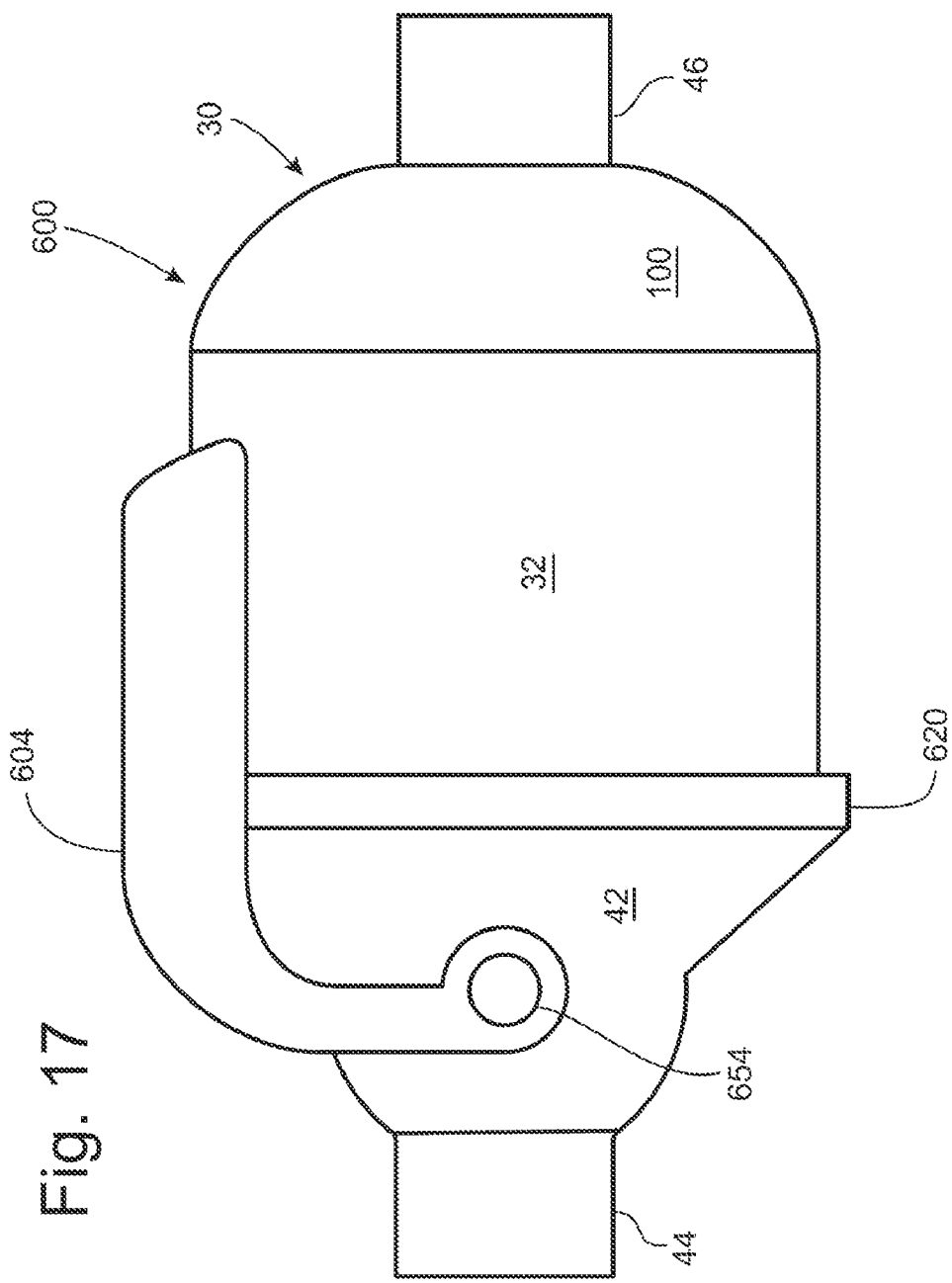
FIG. 17 is a side view of the embodiment of FIG. 16.
Figure 18:
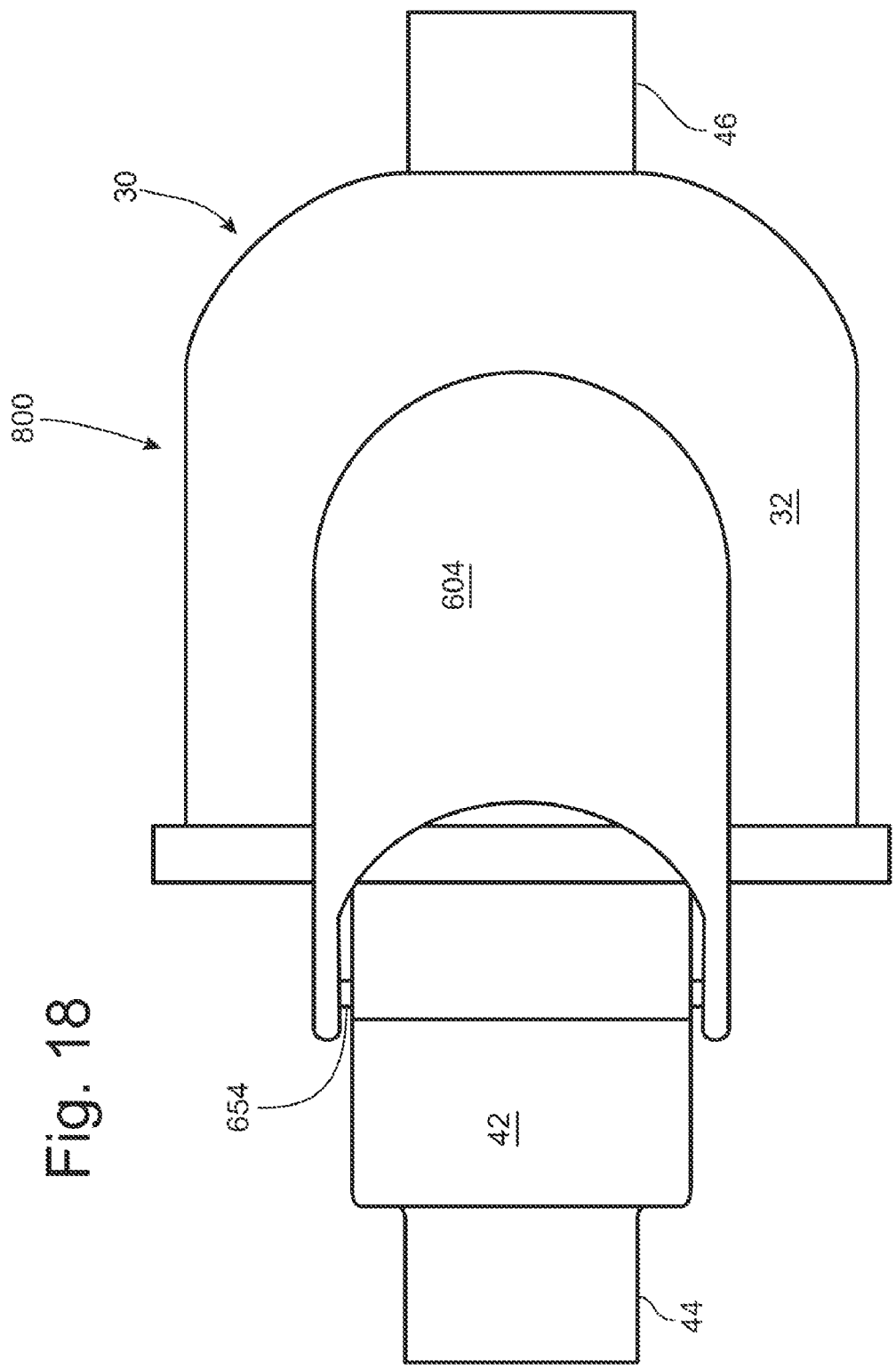
FIG. 18 is a side view of an alternate embodiment of the invention of FIG. 16, where the embodiment of FIG. 18 includes a drum shaped valve in contrast to the embodiment of FIG. 16 that includes a ball valve.

Apparatus 10 is one embodiment of the present invention. Apparatus 10 is shown in FIGS. 1, 2A, 2B, 3A, 3B, 4A, 4B, 5A, 5B, 6A, and 6B. Alternate embodiments of the present invention are apparatus 200, 400, 600, 800 and 900. Apparatus 200 is shown in FIGS. 7A, 7B, 8A, 8B, 9A, 9B, 10A, and 10B. Apparatus 400 is shown in FIGS. 11A, 11B, 12A, 12B, 13A, 13B, 14A, 14B, and 15. Apparatus 600 is shown in FIGS. 16 and 17. Apparatus 800 is shown in FIG. 18. Apparatus 900 is shown in FIGS. 19A, 19B, 20A and 20B.

Common Features of Apparatus 10, 200, 400, 600, 800 and 900

Figure 1:
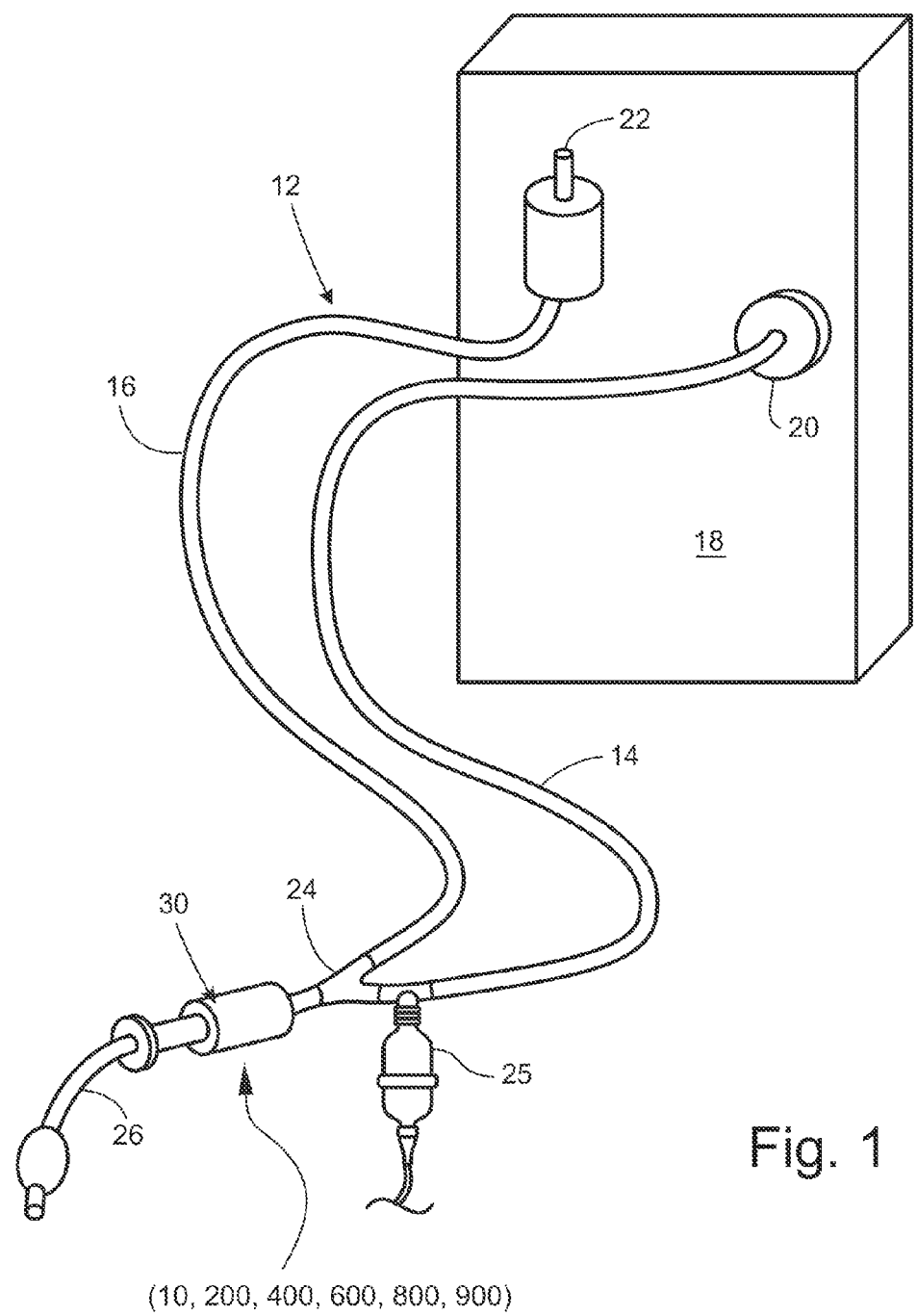
FIG. 1 is a perspective, environmental view of the present HME/MDI apparatus where the apparatus is placed in line in a circuit of a mechanical ventilator.

As shown in FIG. 1, apparatus 10, 200, 400, 600, 800 or 900 is engaged in a mechanical ventilating circuit or system 12 having an inspiratory line 14, an expiratory line 16, a mechanical ventilator 18, a ventilator outlet 20, a ventilator return 22, a wye connection 24, and an endotracheal or tracheostomy tube 26. It should be noted that the mechanical ventilating circuit or system 12 may also be defined to include the mouth, nose, throat and lungs of a patient, any connection such as a pleated flexible tube between the present apparatus and the endotracheal or tracheostomy tube 26, and a nebulizer 25. Specifically, the apparatus 10, 200, 400, 600, 800 or 900 is engaged between the wye connection 24 and the endotracheal or tracheostomy tube 26. Apparatus 10, 200, 400, 600, 800 and 900 can receive medication via an MDI 28, shown in FIG. 15.

Each of the apparatus 10, 200, 400, 600, 800 and 900 includes a housing 30. Each of the housings 30 includes a first or main portion 32 that in turn includes a cylindrical portion (that generally forms a cylinder or a portion of a cylinder). First portion 32 of each of the housings 30 includes a first passage or interior section 34 with HME media 36 therein and a second passage or interior section 38 with an MDI port 40 therein. First portion 32 can be described as the rear portion of the housing or the patient end portion of the housing.

Each of the housings 30 further includes a second portion 42 that is preferably generally spherical (generally forms part of a sphere) but that alternatively may be conical or have a flat end. Second housing portion 42 is or includes a valve for directing fluid flow to the HME passage 34 or the MDI passage 38. In apparatus 200 and 400, the second housing portion 42 is a valve such that the second housing portion 42 rotates relative to the first housing portion 32 for directing fluid flow to the HME passage 34 or the MDI passage 38. In apparatus 10, 600, 800, and 900 second housing portion 42 is fixed to first housing portion 32 and second housing portion 42 includes or confronts a valve for directing fluid flow to the HME passage 34 or the MDI passage 38. Second end portion 42 of the housing 30 can be described as the front portion of the housing 30 or the ventilator end portion of the housing 30.

The housing 30 of each of the apparatus 10, 200, 400, 600, 800 and 900 further includes a housing inlet 44 and a housing outlet 46. The inner diameter of the housing inlet 44 is preferably less than the inner diameter of the housing outlet 46. The housing inlet 44 includes laterally opposing sections 48, 50. The housing outlet 46 includes laterally opposing sections 52, 54. First housing portion 32 includes an endless generally cylindrical sidewall 56 (or cylindrical portion 56) having laterally opposing portions 58, 60, where a length between the laterally opposing portions 58, 60 of the sidewall 56 is greater than a length between the laterally opposing sections 48, 50 of the housing inlet 44 and is further greater than a length between the laterally opposing sections 52, 54 of the housing outlet 46. Each of the housing inlet 44 and housing outlet 46 is adapted for engagement with the mechanical ventilator circuit 12 or tracheal or endotracheal tube. Housing inlet 44 can be engaged to wye connection 24. Housing outlet 46 can be engaged to tracheal or endotracheal tube 26. The housing inlet 44 and housing outlet 46 are in fluid communication with each other via the HME passage 34 or the MDI passage 38 such that, when the valve is fully closed, the HME passage 34 is in fluid communication with each of the housing inlet 44 and housing outlet 46 at one time and the MDI passage 38 is in fluid communication with each of the housing inlet 44 and housing outlet 46 at a different time. When the valve is partially open, HME passage 34 and MDI passage 38 are in fluid communication with each of the housing inlet 44 and housing outlet 46 at the same time.

In each of the embodiments 10, 200, 400, 600, 800 and 900, MDI port 40 includes a receptor or seat portion 62 and a conduit portion 64. An inlet 66 (shown in FIG. 15) is formed in the seat portion 62 and runs partially into the conduit portion 64. Inlet 66 terminates at an annular shoulder 68 of the conduit portion 64. Inlet 66 receives a stem 70 of MDI 28 and annular shoulder 68 receives a distal end of stem 70 such that, when stem 70' is pushed against annular shoulder 68, the stem 70 is relatively retracted into the MDI housing to open a valve in the MDI and release medication from the MDI 28 to a main conduit 72 of conduit portion 64. Medication then flows through main conduit 72 and then exits an outlet 74 of conduit portion 64 and enters the MDI passage 38 of housing 30. Seat portion 62 is engaged to the exterior of first housing portion 32 and is shaped in the form of a disk. Conduit portion 64 extends inwardly from the seat portion 62 and terminates in generally a medial portion of the MDI passage 38.

In each of apparatus 10, 200, 400, 600, 800 and 900, HME passage or first interior section 34 is disposed in parallel with MDI passage or second interior section 38. Further, in each of apparatus 10, 200, 400, 600, 800 and 900, HME passage or first interior section 34 is lateral of MDI passage or second interior section 38. Yet further, in each of apparatus 10, 200, 400, 600, 800 and 900, HME passage or first interior section 34 is immediately lateral of MDI passage or second interior section 38.

In each of apparatus 10, 200, 400, 600, 800 and 900, a valve confronts one of the housing inlet 44 and housing outlet 46 such that fluid can be conveyed from one of the housing inlet 44 and housing outlet 46 selectively into one of the HME passage 34 or MDI passage 38 and/or such that fluid flow can be minimized into at least one of the HME passage 34 or MDI passage 38. In each of apparatus 10, 200, 400, 600, 800 and 900, the valve is engaged with, or more preferably is one-piece with, an arm that alternately blocks off and uncovers the MDI port 40. In apparatus 10, 600, 800 and 900, the valve and arm rotate together at the same time on a lateral axis, and the first housing portion 32 is fixed relative to the second housing portion 42. In apparatus 200 and 400, the valve and arm rotate together at the same time on a longitudinal axis, and such rotation is effected by rotating the second housing portion 42 relative to the first housing portion 32. In each of the apparatus 10, 200, 400, 600, 800 and 900, the arm controls the opening and closing of the valve relative to the HME passage 34 and MDI passage 38 such that positions of the arm can communicate to a caregiver open and closed positions of the valve in the housing 30 relative to the HME passage 34 and MDI passage 38.

In each of the apparatus 10, 200, 400, 600, 800 and 900, the arm includes a portion confronting the MDI port 40, specifically confronting the MDI seat portion 62, when the valve is closed relative to the MDI passage 38 and open relative to the HME passage 34. Such portion of the arm is out-of-the-way of the MDI seat portion 62 when the valve is open relative to the MDI passage 38 and closed relative to the HME portion.

In each of apparatus 10, 200, 400, 600, 800 and 900, the MDI passage 38 is a chamber, or empty chamber, for receiving a plume of medication from the MDI 28.

In each of apparatus 10, 200, 400, 600, 800 and 900, a filter may be disposed downstream from the housing inlet 44 and upstream from the HME passage 34 and MDI passage 38. In apparatus 10, 200, 400, 600, 800 and 900, the filter may be disposed between the valve and the HME and MDI passages 34, 38. In apparatus 400, the filter may be disposed between the housing inlet 44 and the valve openings. The filter has openings sufficiently large to smoothly let gas, such as air, flow therethrough. The filter has openings sufficiently small to act as a bacterial/viral filter. In each of apparatus 10, 200, 400, 600, 800 and 900, the filter is optional.

In each of the apparatus 10, 200, 400, 600, 800 and 900, first housing portion 32 includes a cylindrical portion 56 and a distal end portion 100 that are integral with each other. The distal end portion 100 is disposed between the endless sidewall 56 (or cylindrical portion 56) and the housing outlet 46. Distal end portion 100 is generally spherical (generally forms a portion of a sphere) and is integral and one-piece with the housing outlet 46 and endless sidewall 56.

In each of the apparatus 10, 200, 400, 600, 800 and 900, inlet 44 (or its respective swivel portion) is an isotaper round inlet with a 15 mm outside diameter and outlet 46 (or its respective swivel portion) is an isotaper round outlet with a 15 mm inside diameter. It should be noted that, in apparatus 200 and 400 where swivel portions can be engaged to the inlet 44 and outlet 46, only one swivel portion can be used, with such single swivel portion preferably engaged to the inlet 44.

In each of the apparatus 10, 200, 400, 600, 800 and 900, a divider 102 is present. Divider 102 can be a flat form, as in apparatus 10, 200, 600 and 800. Divider 102 can be a cylinder, as in apparatus 400 or 900. Or, as described with reference to apparatus 10, 200, 600, 800 and 900, divider 102 can be of a tubular or cylindrical form or of other variable shape, where the axis of such cylinder is aligned or offset from the axis of the housing 30 as a whole. An alignment is shown in FIG. 19A where tube 912 is the divider. The divider can form a V-shape in section if desired. Such a V-shape is shown in phantom in FIG. 5A (divider 102). The interior of the V-shape can be used as either the HME section 34 or the MDI section 38, with such interior preferably being used as the MDI section 38 because of the less volume occupied by such interior. The exterior of the V-shape can be used as either the HME section 34 or the MDI section 38, with such exterior preferably being used as the HME section 34 because of the greater volume occupied by such exterior. The divider 102 can be structured in many shapes and the attendant volume of the space occupied by the HME section 34 and MDI section 38 can be different.

In each of the apparatus 10, 200, 400, 600, 800 and 900, the divider 102 extends toward the outlet 46 and terminates at a longitudinal point about where the cylindrical portion 56 ends and the distal end portion 100 begins. If desired the divider 102, as shown in phantom in FIG. 8B, can extend beyond where the cylindrical portion 56 ends and into the distal end portion 100. The divider 102 terminates short of the outlet 46. The HME passage 34 and MDI passage 38 are thus in communication in the area at an end of the divider 102 and in the area confronting the outlet 46. Divider 102 can further be longitudinally wedge-shaped to allow more space to be dedicated to the HME or MDI as desired, where the point of the wedge is pointed toward the outlet.

In each of apparatus 10, 200, 400, 600, 800 and 900, danger is eliminated that flow is decreased or absent due to the position of the valve. In other words, as to apparatus 10, if the valve is open 50% to the MDI section, flow is also 50% through the HME section, or if the flow is only 40% open to the MDI section, flow is 60% through the HME section, and so on. As to apparatus 200, as the HME port 268 of the second housing portion 42 begins to close, the MDI port 269 of the second housing portion 42 beings to open. In other words, as to apparatus 200, if the valve is 50% open to the MDI section, the valve may be open only 49.5% to the HME section. Engineering tolerances or safeguards account for the minimal reduction in fluid flow. As to apparatus 400, the position of the HME ports 432 of second housing portion 42 and the position of their corresponding HME inlets 410 of the first housing portion 32 are set relative to the position of the MDI ports 434 of the second housing portion 42 and the MDI inlets 408 of the first housing portion 32 such that, immediately upon rotation of the housing portions 32, 42 relative to each other, the HME inlets 410 begin to close (or open) and the MDI inlets 408 being to open (or close). In other words, as to apparatus 400, if the valve is 50% open to the MDI section, the valve may be open only 49.5% to the HME section. Engineering tolerances or safeguards account for the minimal reduction in fluid flow. As to apparatus 600, the valve seat portions 608, 610 and 612 may slightly overlap with valve walls 644 and 646 such that if the valve is 50% open to the MDI section, the valve may be open only 49.5% to the HME section. As to apparatus 900, the HME section 34 is always open.

Each of apparatus 10, 200, 400, 600, 800 and 900 may be in fluid communication with a nebulizer 25, as shown in FIG. 1. The nebulizer 25 is engaged to the mechanical ventilator circuit upstream from the apparatus 10, 200, 400, 600, 800 or 900 in the inspiratory line 14 such that the nebulizer 25 is in fluid communication with the inlet 44 of the housing 30. The nebulizer 25 discharges medication into the inlet 44, through the second interior MDI section 38, and out of the outlet 46. A conventional HME must be taken out of the mechanical ventilator circuit in order to deliver any medication, including nebulizer based medication, to the patient. The present apparatus 10, 200, 400, 600, 800 and 900 may remain in line when medication such as nebulizer based medication is desired to be delivered because of the presence of the MDI conduit or interior section 38.

Apparatus 10 Specifically

Figure 4A:
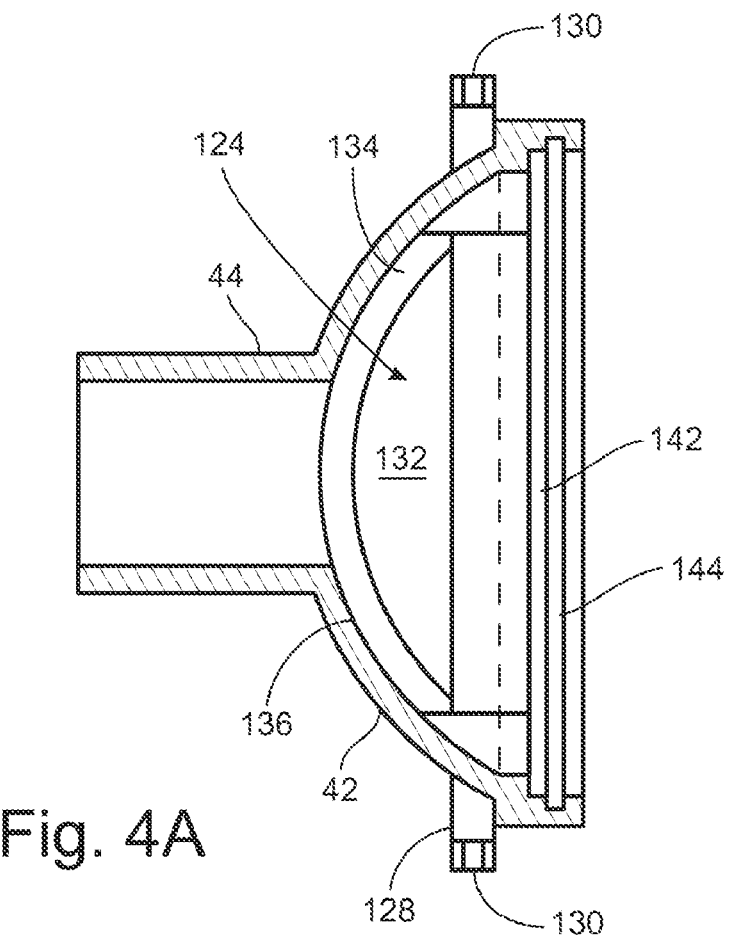
FIG. 4A is a plan view of a portion of the HME/MDI apparatus of FIG. 3A and shows a valve that is manipulated to a) open the HME passage and close the MDI passage at the same time, and b) close the HME passage and open the MDI passage at the same time.
Figure 4B:
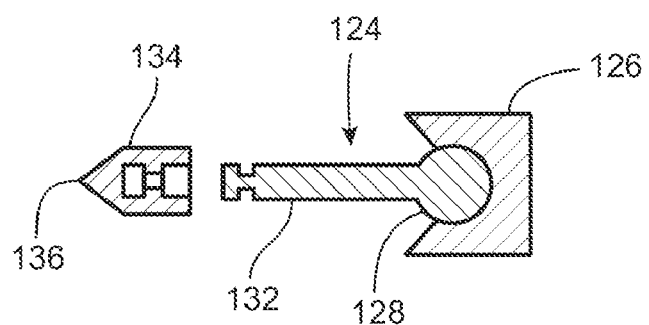
FIG. 4B is a side, partially sectional view of the valve of FIG. 4A.
Figure 5A:
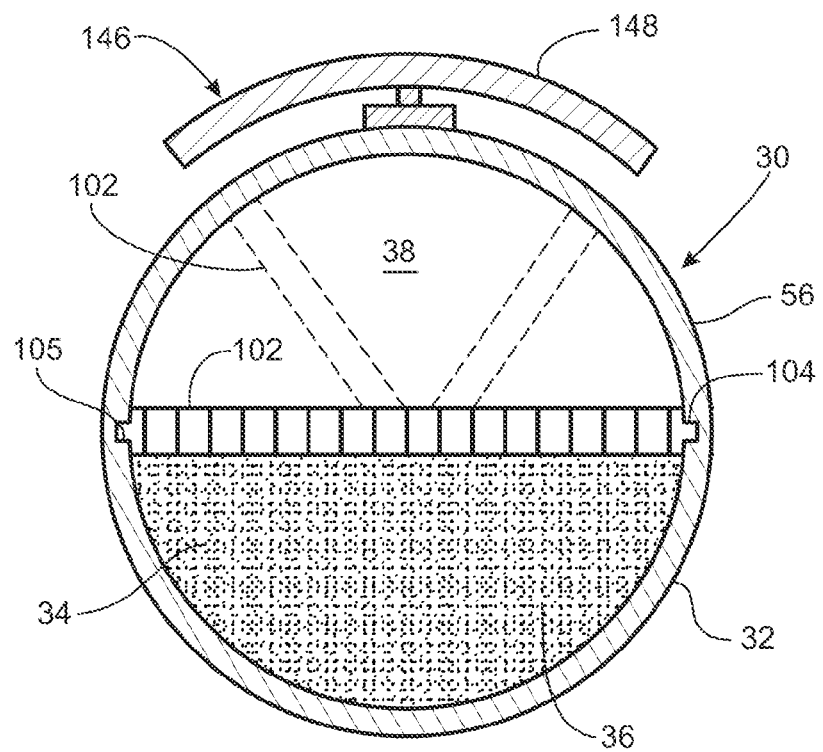
FIG. 5A is a section at lines 5A-5A of FIG. 3A and shows a portion of the arm for simultaneously blocking off the MDI port and turning the valve for closing the MDI passage, where the portion of the arm is cylindrical for conforming to the housing of the HME/MDI apparatus, and further shows interior HME and MDI sections separated by a divider.

With particular reference to apparatus 10, as shown in FIGS. 2A, 2B, 3A, 3B, 4A, 4B, 5A, 5B, 6A and 6B, first housing portion 32 includes a divider 102. The divider 102 is generally a rectangular plastic piece with a tongue 104 extending from three sides of the divider. The tongues 104 of two opposite sides, as shown in FIG. 5A, mate with slots 105 formed diametrically in the interior face of the sidewall 56. A third side of divider 102, the side confronting the housing inlet 44, includes a tongue for mating with the filter. A fourth side, the side confronting the housing outlet 46, has no tongue. The divider 102 separates the HME passage 34 from the MDI passage 38. The divider 102, along with sidewall 56, also forms an HME inlet 106 and an MDI inlet 108. The divider 102, along with sidewall 56, also forms an HME outlet 110 and an MDI outlet 112.

Second housing portion 42 of apparatus 10 snaps over an annular ridge 113 integral with the sidewall 56 such that first housing portion 32 and second housing portion 42 are unitary (form generally a unit where the portions 32 and 42 are fixed and static relative to each other).

Figure 6A:
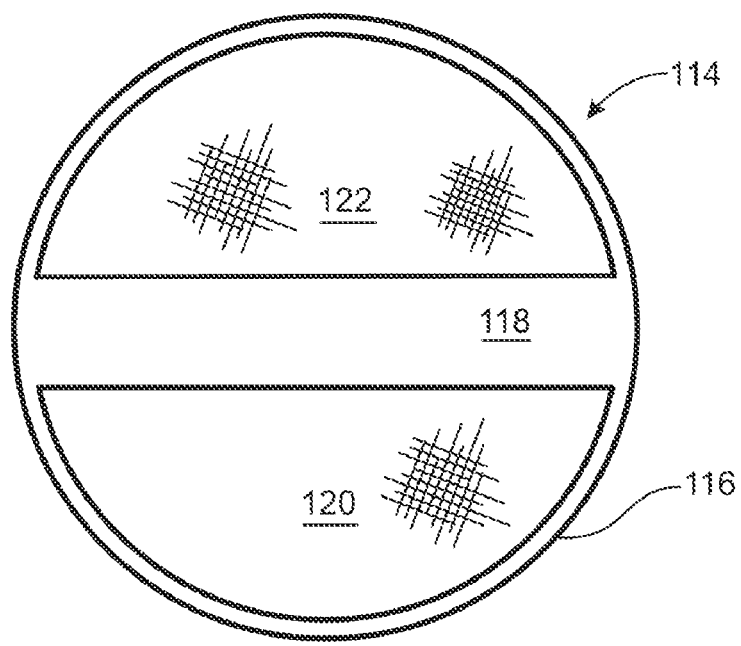
FIG. 6A is a front plan view of an optional filter for the HME/MDI apparatus of FIG. 3A.
Figure 6B:
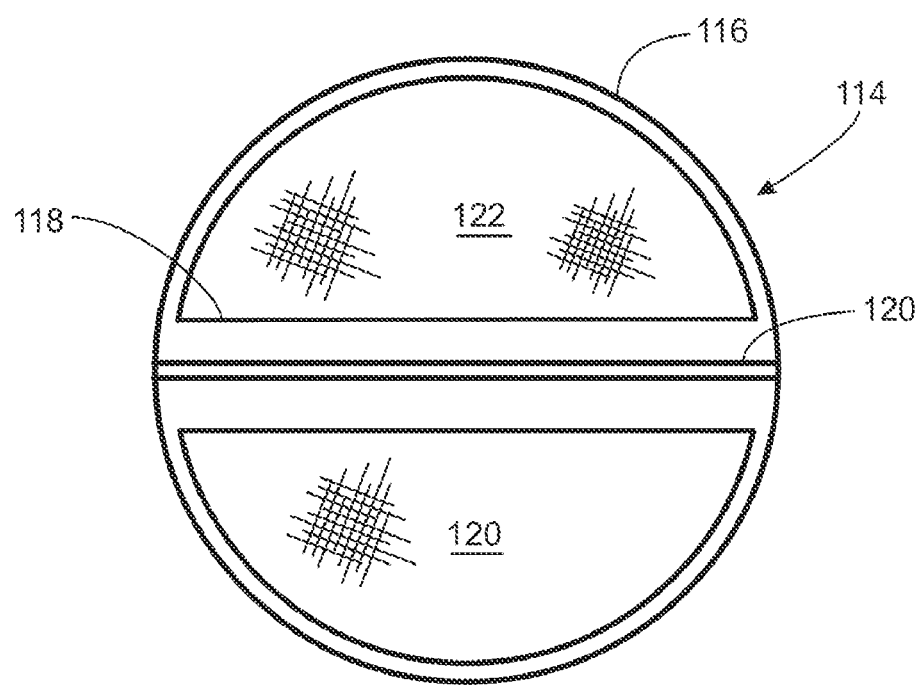
FIG. 6B is a rear plan view of a filter for HME/MDI apparatus of FIG. 3A.
Figure 8A:
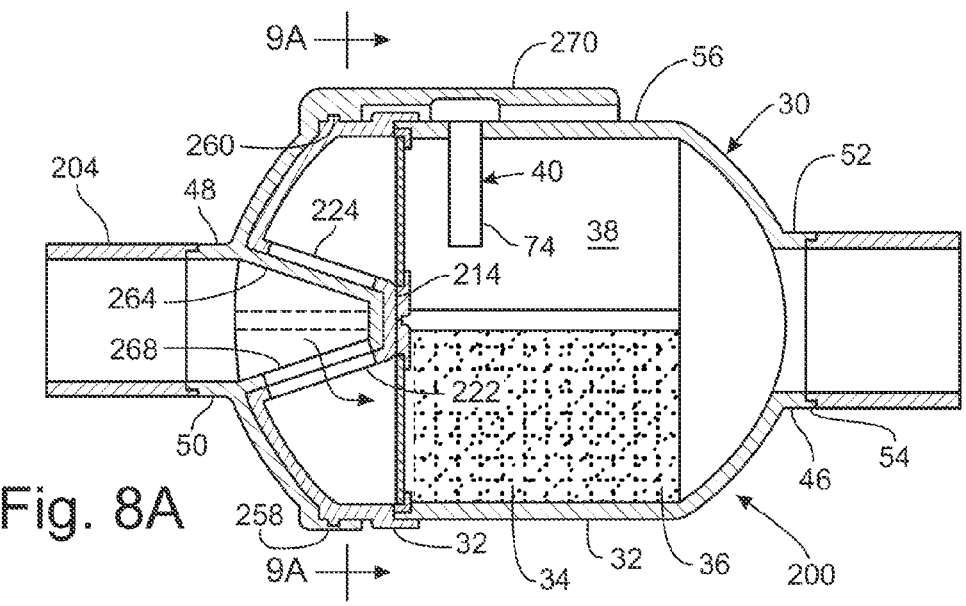
FIG. 8A is a section view of the HME/MDI apparatus of FIG. 7A, where the HMI passage is open and the MDI passage is closed via rotation of a valve, and where the MDI port blocked off via an arm that is one-piece with the valve.
Figure 8B:
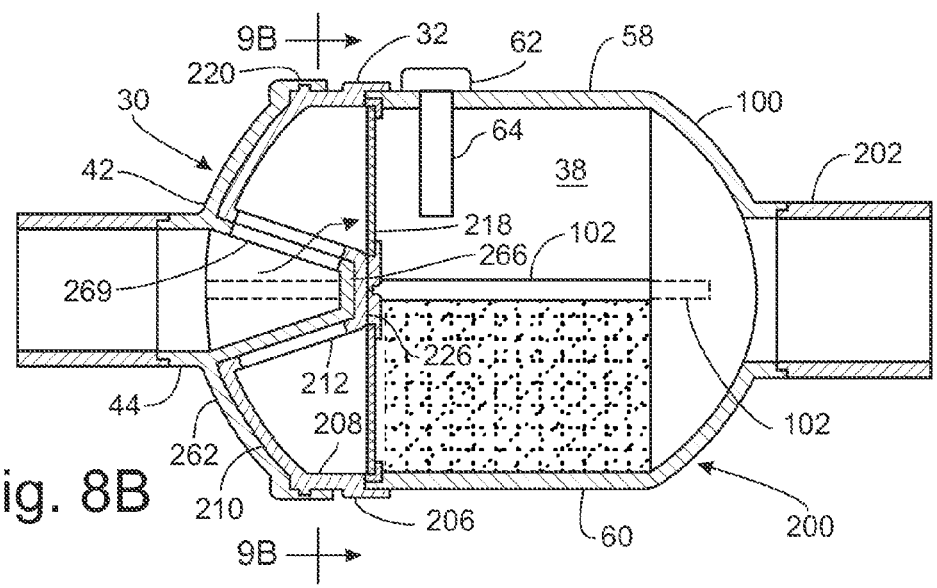
FIG. 8B is a section view of the HME/MDI apparatus of FIG. 7B, where the HMI passage is closed and the MDI passage is open via rotation of the valve, and where the MDI port is accessible via the arm being rotated out-of-the-way to expose the MDI port.

Prior to the housing portions 32, 42 being snapped together, a filter 114 is pinched between the housing portions 32, 42. As shown in FIGS. 6A and 6B, filter 114 includes an annular support ring 116. The support ring 116 is pinched between annular ends of housing portions 32, 42. A laterally extending support 118 is integral with support ring 116 and extends diametrically across ring 116. Support 118 includes a slot 120 for receiving tongue 104 of divider 102. Filter 114 includes a first perforated port 120 for confronting the HME inlet 106 and a second perforated portion 122 for confronting the MDI inlet 108.

As shown in FIGS. 4A and 4B, second housing portion 42 of apparatus 10 includes a valve 124. Valve 124 is a vane valve or a vane like valve. Valve 124 includes a laterally extending base 126 extending to diametrically opposing portions of second housing portion 42. Valve 124 further includes a rod or shaft 128 pivotally mounted in the base 126 and sealingly extending out of second housing portion 42. At each of its outer end portions, shaft 128 includes an interlock or cross fitting end portion 130. Valve 124 further includes a rigid vane portion or flat piece 132 integral with and extending from the shaft 128. Vane portion 132 is generally semicircular in shape and includes a semicircular edge gasket 134 that is permanently engaged or replaceable and that can snap onto the vane portion 132. Semicircular edge gasket 134 includes a tapered edge 136 that sealingly engages an interior surface of second housing portion 42 such that the vane portion 132 can seal one of the HME passage 34 and MDI passage 38 against flow of gas.

As shown in FIGS. 3A and 3B, vane portion 132 rotates between an MDI stop 138 and an HME stop 140. Each of the stops 138, 140 confronts the housing inlet 44 such that a distance between stops 138 and 140 is only slightly greater than the diameter of the housing inlet 44 and such that a gas flow from inlet 44 flows smoothly into one of the HME passage 34 and MDI passage 38. Each of the stops 138, 140 can be semicircular in shape and run from about the housing inlet back to the filter 114 such that the tapered edge 136 confronts and abuts the stops 138, 140 along substantially the entire length of tapered edge 136.

As shown in FIG. 4A, second housing portion 42 includes an annular groove 142 for engaging the support ring 116 of filter 114 and an annular groove 144 for receiving the annular ridge 113 of first housing portion 32.

Interlocking end portion 130 of valve 124 interlocks with an arm 146 that blocks off and uncovers MDI port 40 such that motion of the arm 146 in turn translates into motion of valve 124 and such that motion of valve 124 translates into motion of the arm 146.

Arm 146 includes a portion 148 formed that is generally cylindrical in shape (generally forms a portion of a cylinder). Arm portion 148 blocks off and uncovers MDI port 40.

Figure 2A:
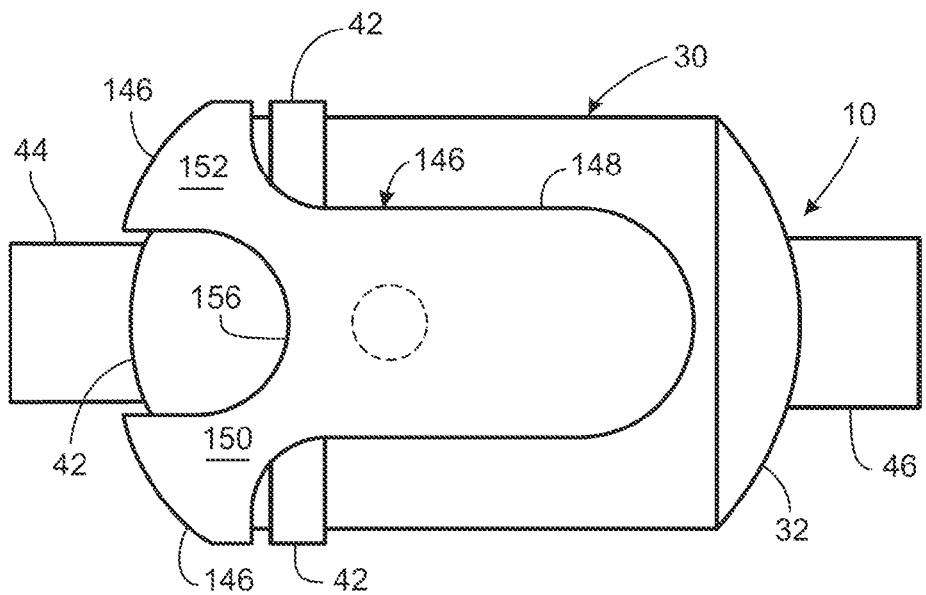
FIG. 2A is top plan view of an embodiment of the HME/MDI apparatus showing an arm blocking off the MDI port.
Figure 5B:
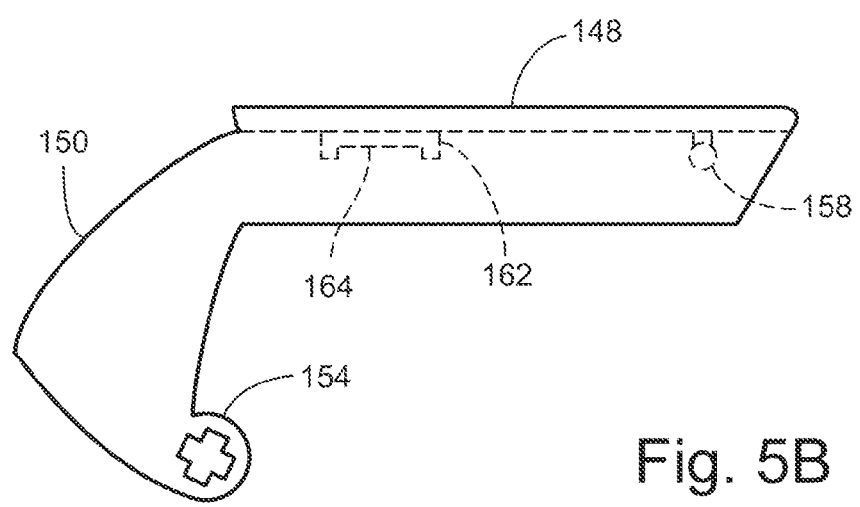
FIG. 5B is a side view of the arm of FIG. 5A that at the same time blocks off the MDI port and turns the valve to close off the MDI passage.

Arm 146 is bifurcated so as to have right side and left side integral arm extensions 150, 152. Arm extension 150 is shown in FIGS. 2A and 5B. Arm extension 152 is shown in FIGS. 2A, 3A and 3B. End portions 154 of arm extensions 150, 152 engage the interlocking ends 130 of shaft 128 such that a swinging of arm 146 swings the flap 132 of valve 124. Arm portion 148 includes at a proximal end portion a stop 156 (shown in FIGS. 2A and 3B), disposed between the arm extensions 150, 152, so as to terminate a swinging of arm 146 in one direction when arm stop 156 abuts inlet 44. When stop 156 abuts inlet 44, valve 124 engages HME stop 140 so as to fully open the MDI passage 38 and fully close HME passage 34. When arm portion 148 confronts and covers up MDI port 40, valve 124 engages MDI stop 138 so as to fully open the HME passage 34 and fully close the MDI passage 38.

Arm portion 148 includes on its underside at a distal end portion a ball snap 158 that snaps into a receiver 160 fixed to the sidewall 56. Arm portion 148 includes a seat cover 162 fixed to its underside that confronts and sealingly engages seat portion 62 having inlet 66 that communicates with MDI passage 38. Seat cover 162 seals inlet 66 against gas flow to or from inlet 66. Seat cover 162 includes a depression 164 in the shape of a disk to mate with the disk shaped seat portion 62.

It should be noted that apparatus 10 can be described as an embodiment having a lever action, with the lever action being about a laterally extending axis. Ventilator end housing 42 (rear housing 42 or second housing portion 42) has a 15 mm outside diameter at the inlet 44. Inlet 44 is an isotaper round inlet, and second housing portion 42 extends from the round inlet 44 to the full diameter of the first housing portion 32 in a hemispherical fashion. Fixed immediately inside the rear section 42 are the two stops 138, 140. The stops 138, 140 are vertically offset from each other. The stops 138, 140 conform to the curve of the second housing portion 42. A semi-circular vane or valve 124 is fixed to an axis or laterally extending shaft 128, which in turn is enclosed in a strut 126. Strut 126 is fixed laterally and diametrically in second housing portion 42 such that strut 126 is positioned midway between a top and bottom of the second housing portion 42. Vane or valve 124 rotates about ninety degrees, with such movement limited by stops 138, 140. Both end portions of the axis or shaft 128 protrude snugly through holes formed in the wall of second housing portion 42. The holes are sealed against fluid leaks with a film of sealing lubricant. A lever 146 is attached to both ends 130 of the axis or shaft 128. Lever 146 includes arm extensions 150, 152 that are wrapped about the housing 30 so as to follow the curvature of the housing 30. Lever 146 further includes an arm portion 148 that is wrapped about the housing 30 so as to follow the curvature of the housing 30. Arm portion 148 is a lid which covers a portion of the exterior of the apparatus 10. The portion of the housing 30 covered by the lever 146 is colored red and contains language that the HME section 34 is not in use to prevent the MDI section 38 from being inadvertently left open, an action that would greatly reduce heat and moisture delivered to the patient. Movement of the lever 146 is limited by the stops 138, 140 in the housing and also by the protruding inlet 44 of second housing portion 42. A detent mechanism, including ball snap 158 and receiver 160, at the end of the lever 146 locks the lever 146 in a closed position. A cap 162 positioned on the underside of the lever 146 seals the MDI nozzle or port 40 from the outside atmosphere when the lever 146 is in the closed position. An optional filter 114 is disposed on the back of the strut or base 126 and covers, in the nature of a perforated lid, the second housing portion 42. The patient end 32, or first housing portion 32, or front housing end 32, includes a generally cylindrical portion 56. The cylindrical portion 56 mates to the end of rear housing 42 and is carried forward until the cylindrical portion 56 ends in a more or less spherical tapered portion, which in turn leads into a 15 mm inside diameter isotaper outlet 46. First housing portion 32 is divided into two approximately equal sections by a divider 102 which meets the strut 126 of the rear housing portion 42. The divider 102 carries forward towards the patient end until the divider 102 ends at about the longitudinal position where the distal end portion or tapered portion 100 begins and meets the sidewall or cylindrical portion 56. The two divided sections, i.e., the HME passage or section 34 and the MDI passage or section 38, are thus in communication at the front of the patient end. About one half of the front housing 32 is filed with HME medium to the forward end of the divider. About one half of the front housing 32 is an empty receptacle for reception of an MDI plume, with such one half of the front housing 32 having an MDI nozzle 64 protruding through the wall of front housing 32 and disposed near the back end of the front housing 32. The outlet 74 of the MDI nozzle 64 points in the direction of the patient end of the front housing 32, i.e. toward the outlet 46. With the lever 146 in the closed position, the vane 124 is positioned against the stop 138 on the MDI side 38. This directs inspiratory fluid flow through the HME side 34 and through the patient outlet 46. Fluid is prevented from retrograde flow through the MDI side 38 by the vane 124 and by fluid already in the MDI side 38. With the lever 146 in an "up" position, i.e. out-of-the-way of the MDI port 40, the vane 124 is positioned against the stop 140 on the HME side 34. This directs inspiratory fluid flow through the MDI side 38 and through the patient outlet 46. Fluid is prevented from retrograde flow through the HME side 34 by the vane 124 and by fluid already in the HME side 34. In operation, the apparatus 10 is placed between the ventilator wye 24 and the tracheal tube 26 (or endotracheal tube is such is being used). In the HME position where the lever 146 is in the closed position, inspiratory and expiratory fluid flows back and forth through the HME medium, providing previously exhaled heat and moisture back to the patient. To change to the MDI position, the lever 146 is raised completely to the "up" position. This directs all fluid flow through the MDI section. An MDI canister 28 is attached to the MDI nozzle or port 40 in the wall of the apparatus 10 and is discharged, with the discharge action being timed with the beginning of the inspiratory breath delivered by the ventilator. When the prescribed number of MDI discharges is complete, the MDI canister 28 is removed from the nozzle 40, and the lever 146 is returned to the closed position, now directing fluid flow again through the HME section 34.

Figure 2B:
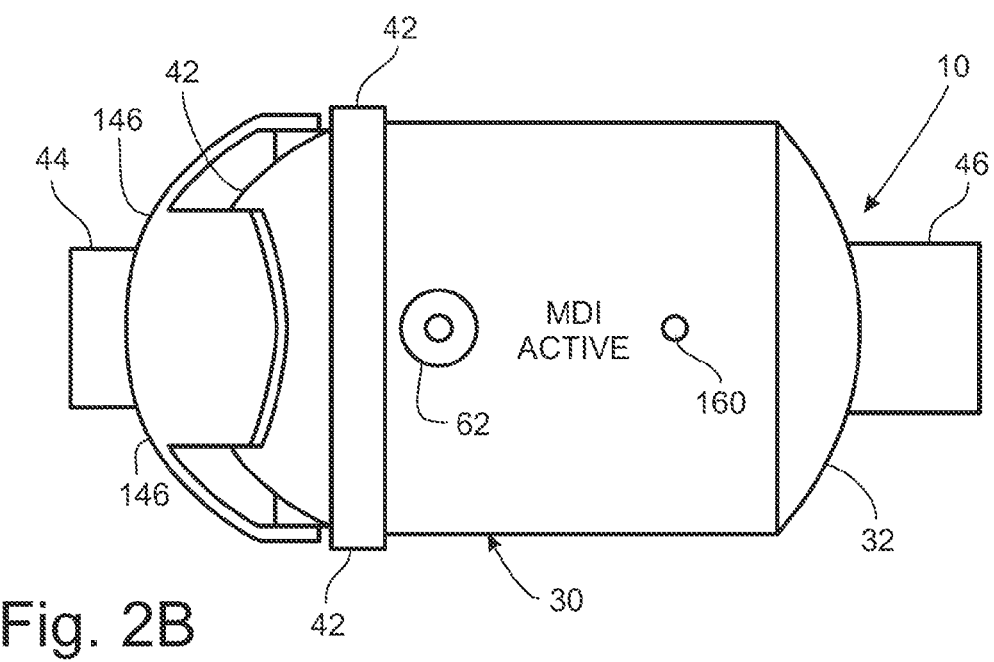
FIG. 2B is a top plan view of the HME/MDI apparatus of FIG. 2A showing the arm rotated out of the way such that the MDI port is accessible.

It should be noted that, as with apparatus 200 and 400, an exterior portion or area of first housing portion 32 of apparatus 10, about MDI port 40, can be colored with a warning color such as red, to warn the practitioner that the MDI section 38 is active. Such an area is covered completely by arm portion 148 when arm portion 148 confronts the MDI port 40. Such an area is uncovered completely by arm portion 148 when the arm portion 148 is out-of-the-way of the MDI port 40. Such an area can also include the indicia "MDI ACTIVE" as shown in FIG. 2B.

Apparatus 200 Specifically

With particular reference to apparatus 200, as shown in FIGS. 7A, 7B, 8A, 8B, 9A, 9B, 10A and 10B, first housing portion 32 of apparatus 200 includes a swivel portion 202 engaged to the outlet 46 and second housing portion 42 includes a swivel portion 204 engaged to the inlet 44 such that housing portion 32, 42 are rotatable relative to each other when connected in line in the mechanical ventilator circuit 12.

First housing portion 32 includes cylindrical portion 56, distal end portion 100, and a valve portion 206. Valve portion 206 is fixed to the cylindrical portion 56 such that there is no rotation between valve portion 206 and cylindrical portion 56. Valve portion 206 includes a cylindrical portion 208 that leads into a spherical portion 210 that leads into a frustoconical portion 212 that leads into a base portion 214. Cylindrical portion 208 may be of another shape, such as a conical shape or frustoconical shape.

Cylindrical portion 208 includes a lip 216 that overlaps and is rigidly affixed to cylindrical portion 56. A filter 218 is pinched between cylindrical portions 56 and 208. Cylindrical portion 208 includes an annular ridge 220 which mates with an annular groove in second housing portion 42 and rotatably engages first and second housing portions 32, 42 to each other.

Spherical portion 210 forms a portion of a sphere and includes an outer surface that slides against an inner surface of second housing portion 42, with such outer and inner surfaces each forming a portion of a sphere such that such outer and inner surfaces can rotate relative to each other. Cylindrical portion 210 may be of another shape, such as a conical shape or frustoconical shape.

Frustoconical portion 212 includes diametrically opposing inlets 222, 224. Inlet 222 is an HME inlet that leads into HME passage 34. Inlet 224 is an MDI inlet that leads into MDI passage 38. Inlets 222, 224 can be seen in FIGS. 8A, 8B, 9A and 9B. It should be noted that frustoconical portion 212 may be of another shape such as a cylindrical shape.

Base portion 214 includes a disk shaped portion 226 (shown in FIG. 8B) and a laterally extending support portion 228. Laterally extending portion 228 can be seen in FIGS. 9A and 9B. Laterally extending portion 228 extends from the disk shaped portion 226 integrally back to frustoconical portion 212, further integrally back to the spherical portion 210, and further integrally back to the cylindrical portion 208 so as to function in the nature of a divider and so as to separate the HMI passage 34 from the MDI passage 38.

Figure 10A:
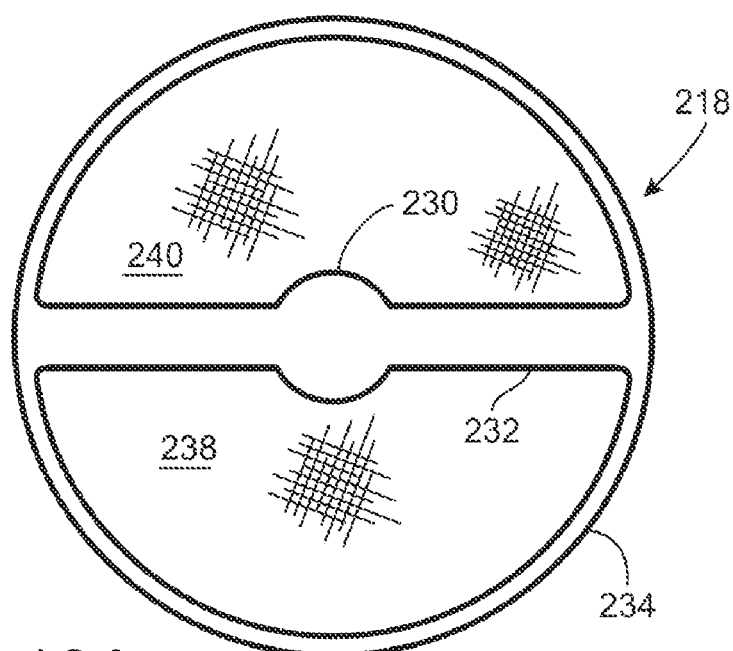
FIG. 10A is a front plan view of the filter of the HME/MDI apparatus of FIG. 8A.
Figure 10B:
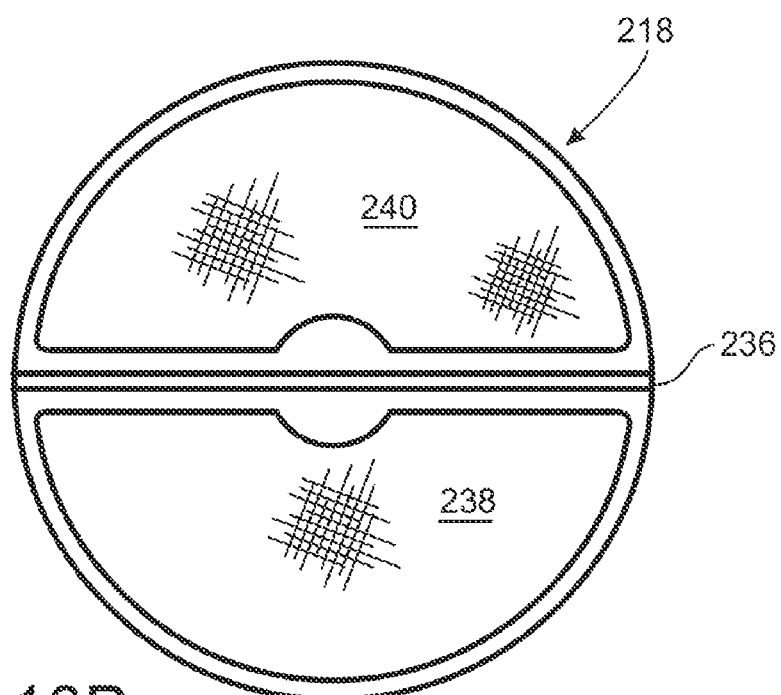
FIG. 10B is a rear plan view of the filter of the HME/MDI apparatus of FIG. 8A.
Figure 11A:
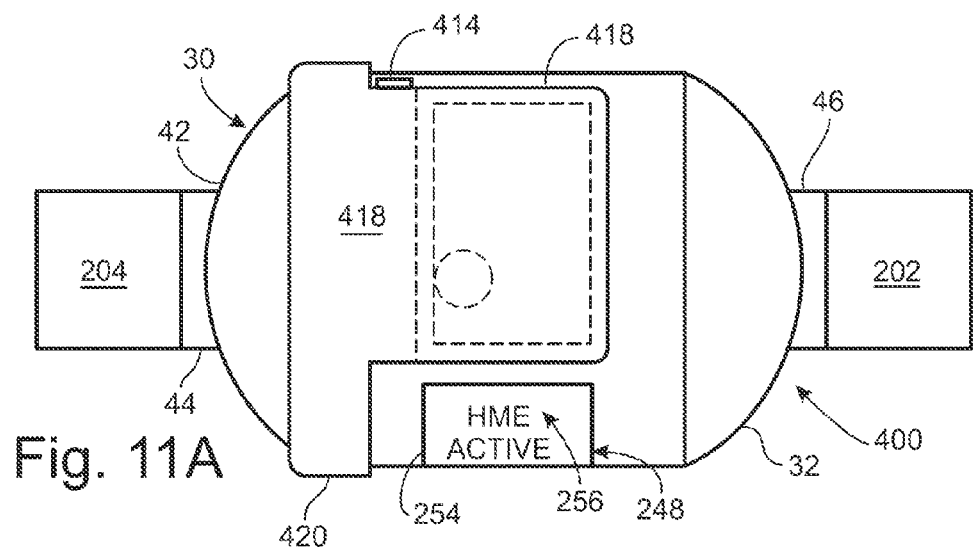
FIG. 11A is a top plan view of an alternate embodiment of the present HME/MDI apparatus showing an arm blocking off the MDI port.
Figure 11B:
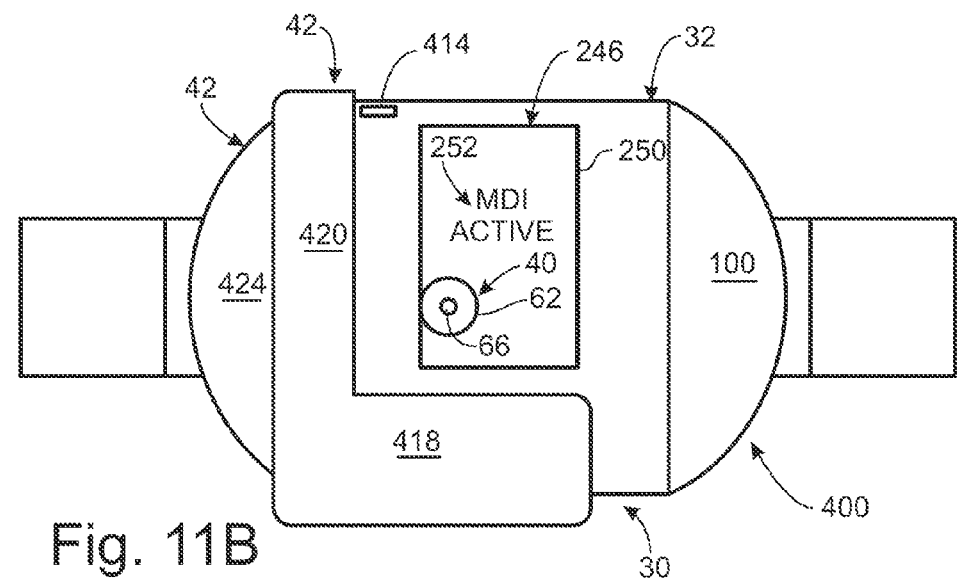
FIG. 11B is a top plan view of an alternate embodiment of the present HME/MDI apparatus showing the arm of FIG. 11A rotated out-of-the-way such that the MDI port is accessible.
Figure 12A:
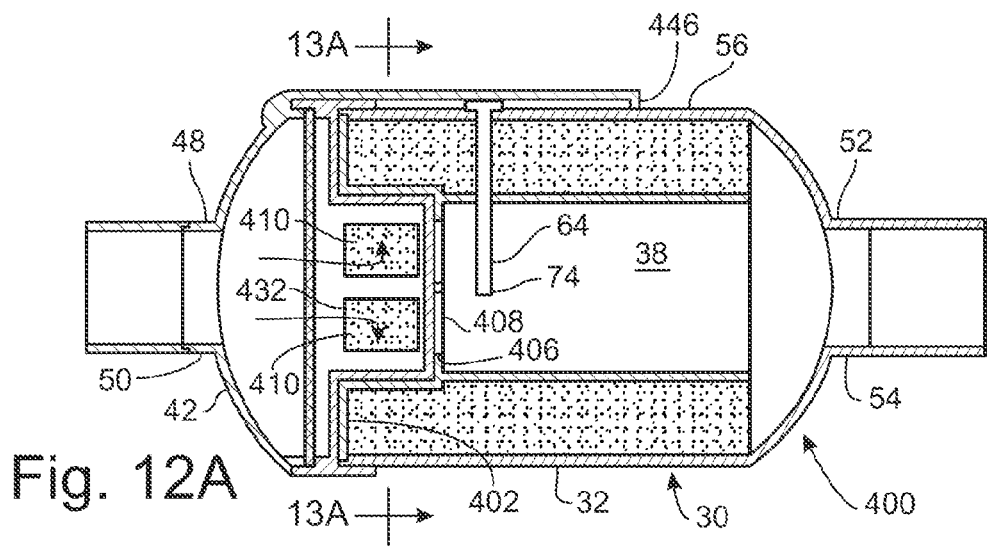
FIG. 12A is a section view of the HME/MDI apparatus of FIG. 11A showing a valve opening the HME passage and closing the MDI passage and showing an arm blocking off the MDI port, where the arm is one-piece with the valve.
Figure 12B:
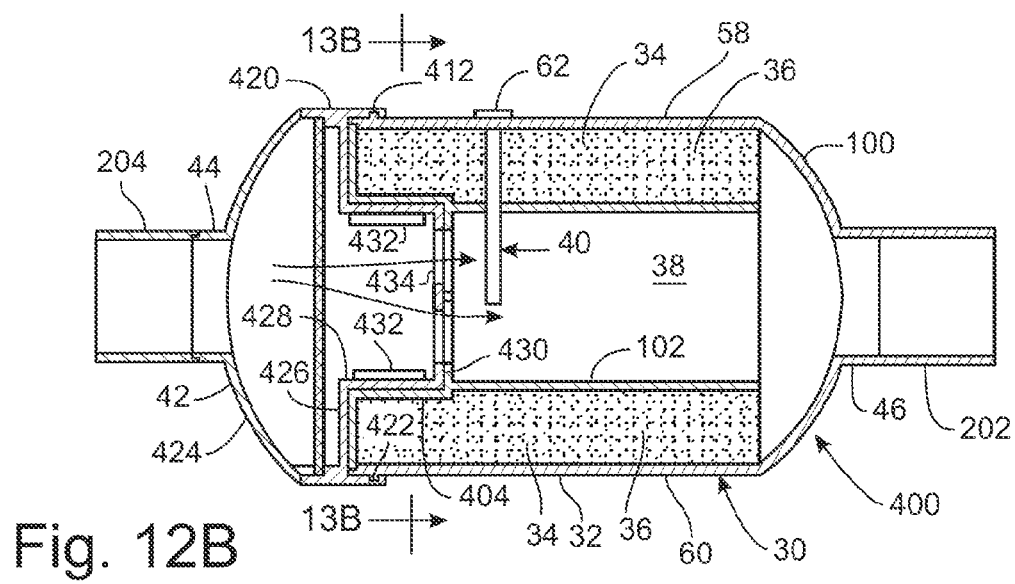
FIG. 12B is a section view of the HME/MDI apparatus of FIG. 11B showing the valve closing the HME passage and opening the MDI passage, and further showing the MDI port being accessible after the arm is rotated out-of-the-way to expose the MDI port.
Figure 13A:
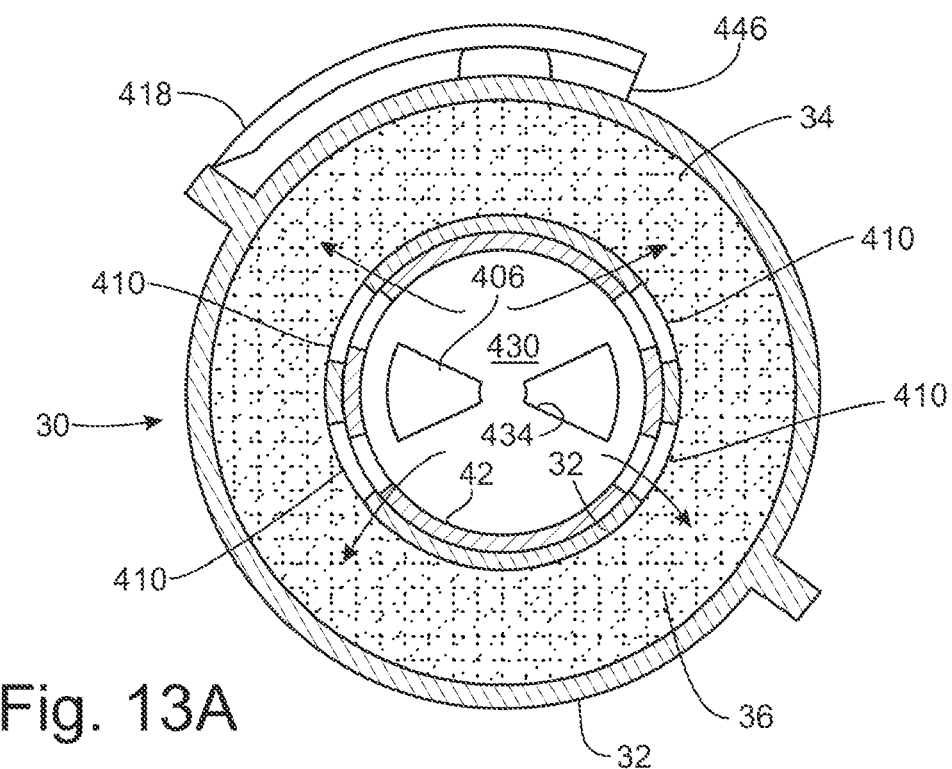
FIG. 13A is a section view at lines 13A-13A of FIG. 12A.
Figure 13B:
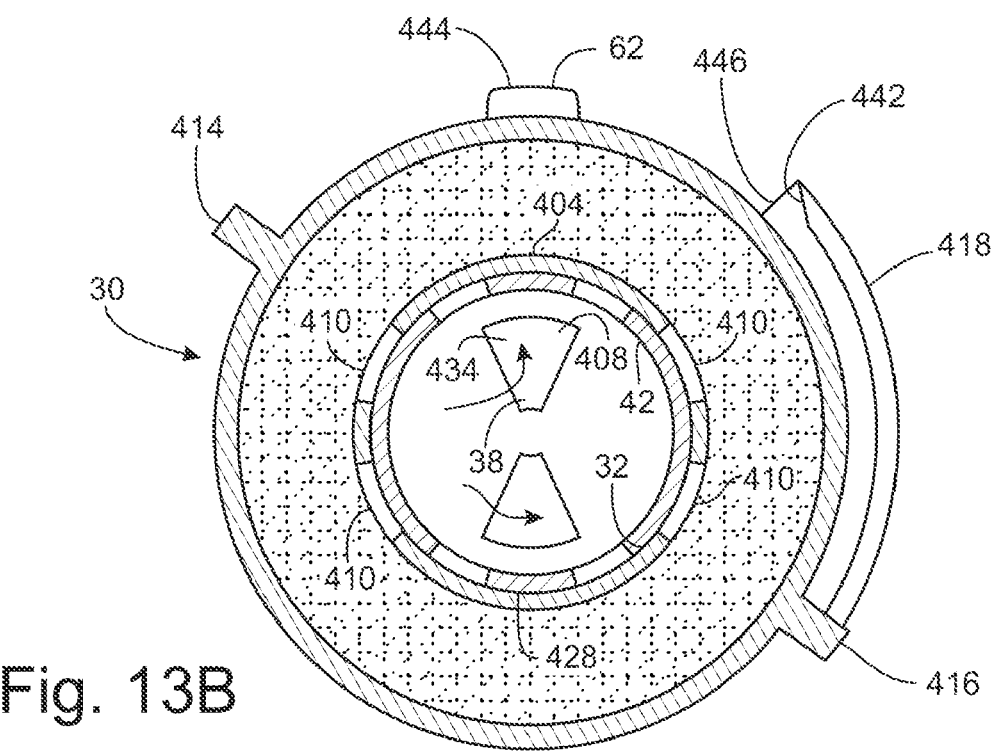
FIG. 13B is a section view at lines 13B-13B of FIG. 12B.

Disk shaped portion 226 and laterally extending support portion 228 confront and abut, respectively, a disk shaped portion 230 of optional filter 218 and a laterally extending support portion 232 of filter 218, as shown in FIG. 10A. Filter 218 further includes an annular ring 234 that is pinched between cylindrical portions 56 and 208 and a slot 236 for receiving the tongue 104 of divider 102, as shown in FIG. 10B. Filter 218 includes a first perforated port 238 for being disposed in the HME passage 34 and a second perforated portion 240 for being disposed in the MDI passage 38.

First housing portion 32 further includes an opening for the conduit or stem portion 64 of MDI port 40.

Figure 9A:
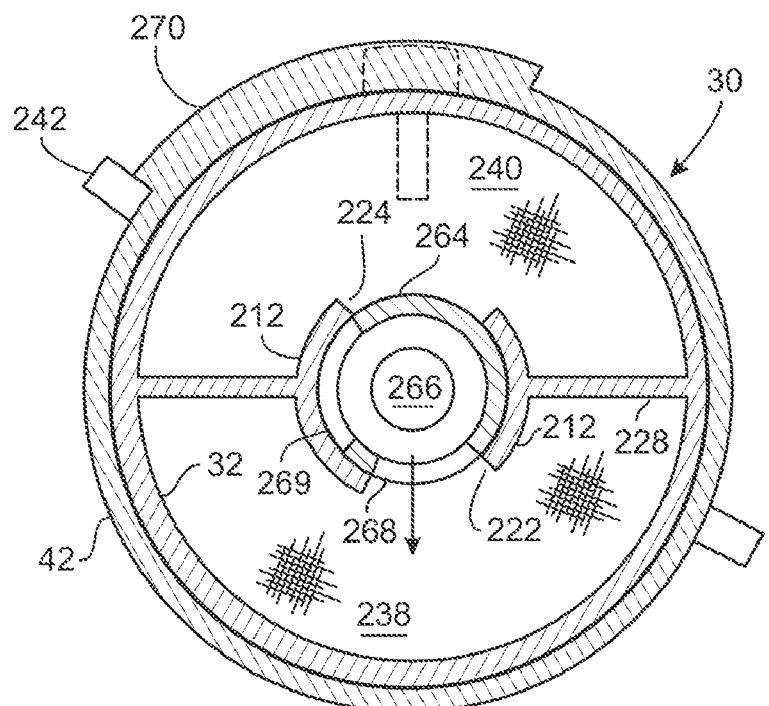
FIG. 9A is a section view at lines 9A-9A of FIG. 8A.
Figure 9B:
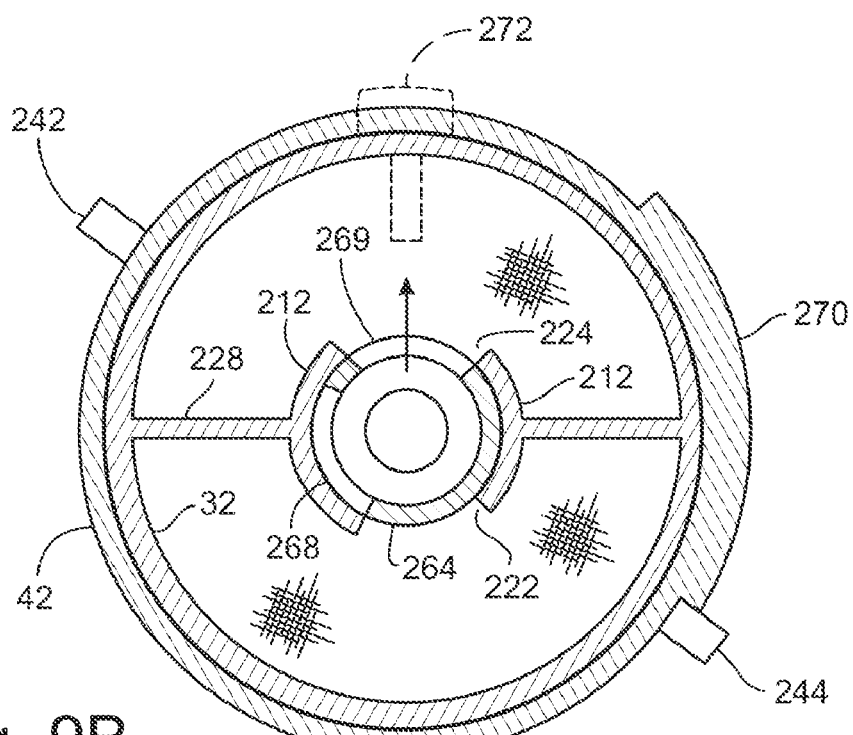
FIG. 9B is a section view at lines 9B-9B of FIG. 8B.

First housing portion 32 further includes a pair of arm stops 242, 244, as shown in FIGS. 9A and 9B. Arm stops 242, 244 are positioned such that ports 268, 269 can fully communicate at different times with each of the HME inlet 222 and MDI inlet 224. Each of the stops 242, 244 is disposed on lip 216 and extends radially from the first housing portion 32. Stops 242, 244 can be seen in FIGS. 7A, 7B, 9A and 9B. Stop 242 engages one side of arm 270. Stop 244 engages the opposite side of arm 270. When stop 242 is being utilized, port 268 is fully open and port 269 is fully closed. When stop 244 is being utilized, port 268 is fully closed and port 269 is fully open. When neither of the stops 242, 244 is being utilized, each of ports 268, 269 is partially open.

First housing portion 32 of apparatus 200 further includes indicia or colored or sign or warning areas 246, 248. Area 246 includes a rectangular boundary 250. Within the boundary 250, the exterior of the first housing portion 32 is colored red, including the seat portion 62 if desired. Within the boundary 250, in a color such as black, the indicia 252 of "MDI ACTIVE" is printed in bold capital letters, warning that the MDI passage 38 is in use. Area 248 includes a rectangular boundary 254. Within the boundary 254, the exterior of the first housing portion 32 is colored green, except for the indicia 256 of "HME ACTIVE" indicating that the HME passage 34 is active.

Second housing portion 42 includes a cylindrical portion 258 having an annular groove 260 for mating with annular ridge 220 of cylindrical portion 208. Second housing portion 42 further includes a spherical portion 262, frustoconical portion 264, and disk shaped portion 266 for confronting, respectively, the spherical portion 210, frustoconical portion 212, and disk shaped portion 226 of first housing portion 32.

Spherical portion 262 of the second housing portion 42 rotates against the spherical portion 210 of the first housing portion 32.

Frustoconical portion 264 has a greater diametrical end confronting and leading in integrally from inlet 44. Frustoconical portion 264 further leads in integrally from spherical portion 262. Frustoconical portion 264 has an HME port 268 and an MDI port 269 for fluid communication, respectively, with the HME inlet 222 and MDI inlet 224 of the first housing portion 32. As HME port 268 begins to rotate away from HME inlet 222, then MDI port 269 begins to rotate into MDI inlet 224 as the first and second housing portions 32 and 42 rotate relative to each other. HME port 268 is out of fluid communication with HME inlet 222 when HME port 268 rotates into a solid portion of frustoconical section 212 and when a solid portion of frustoconical section 264 rotates into HME inlet 222. MDI port 269 is out of fluid communication with MDI inlet 224 when MDI port 269 rotates into a solid portion of frustoconical section 212 and when a solid portion of frustoconical section 264 rotates into MDI inlet 224.

Second housing portion 42 further includes an arm 270 integrally extending from cylindrical portion 208 of second housing portion 42. Arm 270 is cylindrical in shape (forms a portion of a cylinder). Arm 270 includes a longitudinal length of a sufficient greatness to completely cover each of areas 246 and 248 at different times. Arm 270 includes a laterally extending width, or a circumferentially extending width, of a sufficient greatness so as to completely cover each of the areas 246, 248 at different times. Arm 270 is preferably opaque.

Arm 270 is a portion of second housing portion 42 and thus rotates with second housing portion 42. Arm 270 and second housing portion 42 are rotatable relative to first housing portion 32 so as to open and close HME and MDI passages 34, 38 and so as to, at the same time, cover up and uncover corresponding areas 248, 246. Relative rotation of the first and second housing portions 32, 42 comes to a stop when arm 270 hits one of the two stops 242, 244. The underside of arm 270 further seals the seat portion 62 against gas or fluid leakage, and seat portion 62 can have a cylindrical upper or outer side 272, as shown in FIG. 9B to facilitate such a sealing. Arm 270, on its underside, can have a slight depression or receptacle for seat portion 62.

For the HME position where fluid flow is through the HME passage 34, the second housing portion 42 is rotated such that the internal housing frustoconical portion 264 is closed against the MDI inlet 224. Fluid flow from the ventilator 18 is thus directed through swivel portion 204, through HME port 268, through HME inlet 222, through HME filter port 238, through HME passage 34, through outlet 46, and through swivel portion 202. Fluid returning from the patient follows a path exactly opposite of that previously delivered to the patient. As the fluid flows through the HME medium 36, heat and moisture are absorbed by the HME medium 36. A subsequent breath delivered by the ventilator will absorb some of this retained heat and moisture and return it to the patient. In the HME position, the arm 270 automatically covers the MDI area 246 and automatically uncovers the HME area 248.

In the MDI position where fluid flow is through the MDI passage 38, the second housing portion 42 is rotated such that the internal housing frustoconical portion 264 is closed against the HME inlet 222. Fluid flow from the ventilator 18 is thus directed through swivel portion 204, through MDI port 269, through MDI inlet 224, through MDI filter port 240, through MDI passage 38 to pick up medication delivered from MDI canister 28 through MDI port 40, through outlet 46, and through swivel portion 202. In the MDI position, the arm 270 automatically uncovers the MDI area 246 and automatically covers the HME area 248.

In operation, the apparatus 200 is placed between the ventilator wye connector 24 and the tracheal tube 26 (or endotracheal tube). In the HME position, inspiratory and expiratory fluid flows back and forth through the HME medium 36, providing previously exhaled heat and moisture back to the patient. To change to the MDI position, the first and second housing portions 32, 42 are rotated relative to each other on a longitudinally extending axis for about ninety degrees to move HME port 268 out of communication with HME inlet 222 and to move MDI port 269 into communication with MDI inlet 224. This directs all fluid flow to and through MDI passage 38. Then the MDI canister 28 is attached to the MDI nozzle or port 40 in the wall of the apparatus 200 and is discharged, with the discharge action being timed with the beginning of the inspiratory breath delivered by the ventilator. When the prescribed number of MDI discharges is complete, the MDI canister 28 is removed from the nozzle 40, and the housing portions 32, 42 are rotated relative to each other, now directing fluid flow again through the HME passage 34, with arm 248 automatically covering area 246 and sealing off MDI port 40 as the portions 32, 42 are rotated relative to each other.

Apparatus 400 Specifically

With particular reference to apparatus 400, as shown in FIGS. 11A, 11B, 12A, 12B, 13A, 13B, 14A, 14B and 15, first housing portion 32 of apparatus 400 includes a swivel portion 202 engaged to the outlet 46 and second housing portion 42 includes a swivel portion 204 engaged to the inlet 44 such that housing portion 32, 42 are rotatable relative to each other when connected in line in the mechanical ventilator circuit 12.

In apparatus 400, divider 102 is a cylinder such that the HME media 36 takes a cylindrical form about the inner surface of cylindrical portion 56. The MDI passage 38 is found within the divider or cylinder 102.

In apparatus 400, first housing portion 32 includes an annular radially extending portion 402 that leads into an annular longitudinally extending portion 404 that is slightly offset from the cylindrical divider 102. Portion 404 in turn leads into a radially extending disk shaped base portion 406. Portions 404 and 406 together form the shape of a receptacle.

Radially extending disk shaped base portion 406 includes a pair of generally dovetail shaped MDI inlets 408. Inlets 408 are formed diametrically opposite of each other.

Annular longitudinally extending portion 404 includes a set of four HME inlets 410. Two of the inlets 410 confront each other and the other two inlets 410 confront each other such that confronting pairs of inlets 410 are formed. The inlet pairs are formed diametrically opposite of each other and can be seen in FIGS. 13A and 13B.

First housing portion 32 further includes an annular ridge 412 at a proximal end portion of cylindrical portion 56.

First housing portion 32 of apparatus 400 further includes indicia or colored or sign or warning areas 246, 248. Area 246 includes a rectangular boundary 250. Within the boundary 250, the exterior of the first housing portion 32 is colored red, including the seat portion 62 if desired. Within the boundary 250, in a color such as black, the indicia 252 of "MDI ACTIVE" is printed in bold capital letters, warning that the MDI passage 38 is in use. Area 248 includes a rectangular boundary 254. Within the boundary 254, the exterior of the first housing portion 32 is colored green, except for the black indicia 256 of "HME ACTIVE" indicating that the HME passage 34 is active.

First housing portion 32 further includes stops 414, 416 for stopping arm 418 that covers and uncovers MDI port 40. Stop 414 stops arm 418 when the HME passage 34 is in use. Stop 416 stops arm 418 when MDI passage 38 is in use.

Second housing portion 42 includes a cylindrical portion 420 that includes an annular groove 422 for snapping over annular ridge 412 of first housing portion 32. Second housing portion 42 further includes a spherical portion 424 integrally extending from the cylindrical portion 420 and leading into inlet 44. Second housing portion 42 further includes an annular radially extending portion 426 that leads into a longitudinally extending cylindrical portion 428 that leads into a disk shaped radially extending base portion 430. Portions 428 and 430 form the shape of a receptacle. Portions 426, 428, 430 of second housing portion 42 confront and slide against corresponding portions 402, 404 and 406 of first housing portion 32. A medical grade lubricant can be disposed between the first and second housing portions 32, 42 to facilitate rotation therebetween.

Longitudinally extending cylindrical portion 428 includes a set of four HME ports 432. Two of the HME ports 432 confront each other and the remaining two HME ports 432 confront each other such that two pair of confronting HME ports are formed. When the HME passage 34 is in use, HME ports 432 communicate with HME inlets 410.

Disk shaped radially extending base portion 430 includes a pair of dovetail shaped MDI ports 434 formed diametrically opposite of each other in portion 430. When the MDI passage 38 is in use, MDI ports 434 communicate with MDI inlets 408.

Figure 14A:
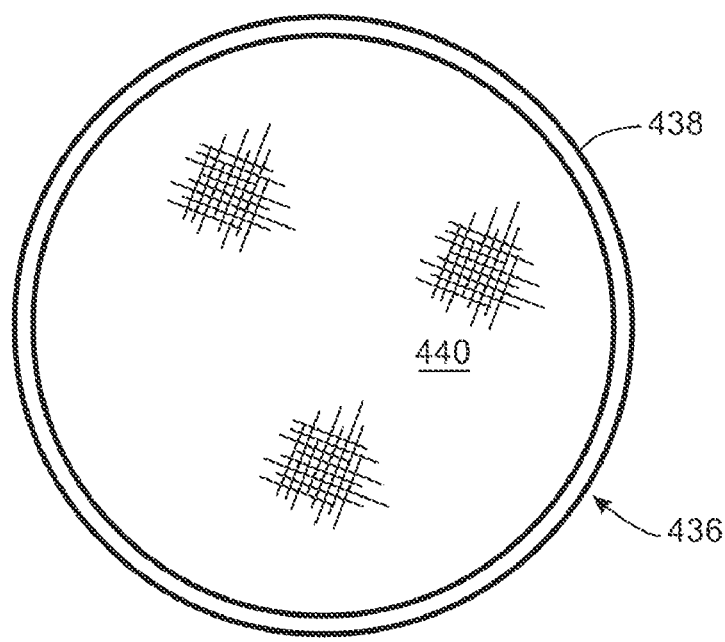
FIG. 14A is a front plan view of the filter of the HME/MDI apparatus of FIG. 12A.
Figure 14B:
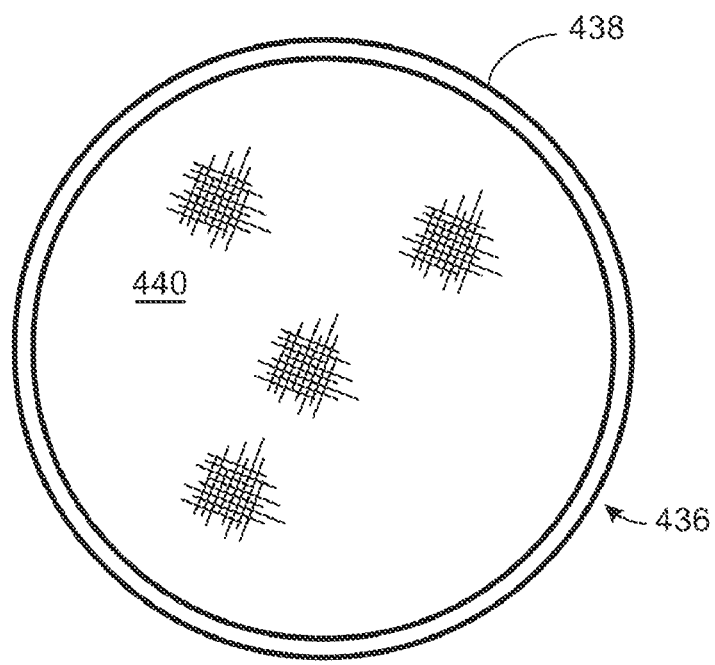
FIG. 14B is a rear plan view of the filter of the HME/MDI apparatus of FIG. 12A.

Second housing portion 42 further includes a filter 436. Filter 436 is engaged by the cylindrical portion 428. As shown in FIGS. 14A and 14B, filter 436 includes a support ring 438 and a perforated filtering portion or media 440 engaged to the support ring 438.

Second housing portion 42 further includes the arm 418. Arm 418 is integral with the cylindrical portion 428. Arm 418 extends longitudinally and circumferentially a sufficient distance to cover areas 246 and 248 at different times. Arm 418 is opaque. Rotation of arm 418 necessarily rotates the second housing portion 42. Rotation of the second housing portion 42 necessarily rotates arm 418.

Arm 418 can have a tapered edge 442 to facilitate a sliding over of arm 418 over seat portion 62. Seat portion 62 includes a cylindrical or rounded upper side 444 to maximize a seal against fluid flow with the underside of arm 418.

Figure 15:
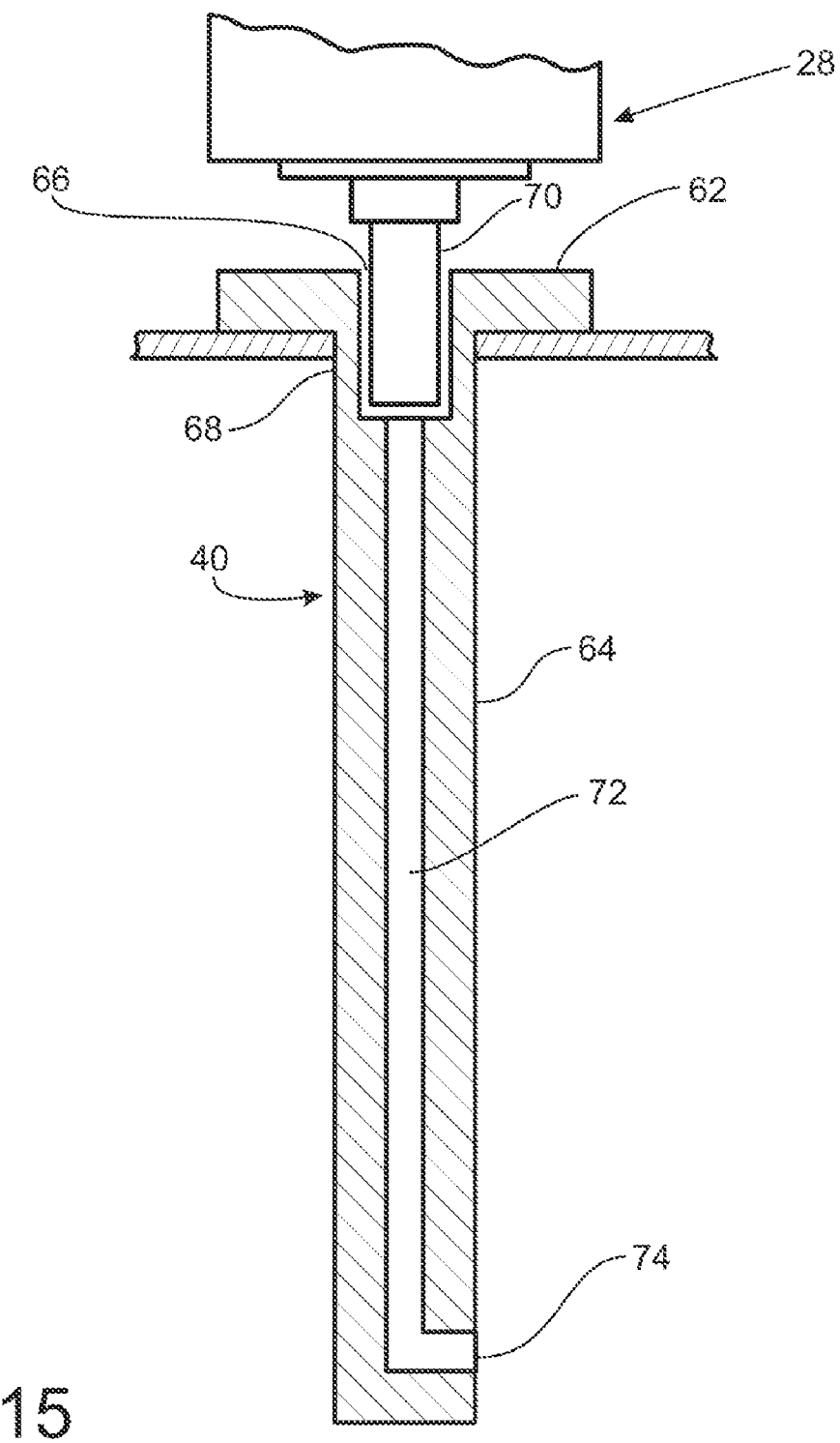
FIG. 15 is a detail section view of the MDI port of the HME/MDI apparatus of FIG. 12A.

FIG. 15 shows the particular MDI port 40 utilized in apparatus 400. That is, conduit portion 64 is of a sufficient length to extend through cylindrical HME passage 34 and into central MDI passage 38. A well or depression could be inserted in the wall of the MDI section to drop the MDI port 40 further into the section.

Arm 418 includes a radially and laterally extending end portion 446 than extends down to the exterior surface of first housing portion 32. End portion 446 aids in stabilizing the arm 418.

For the HME position where fluid flows through the cylindrical HME passage 34 or collar 34 of apparatus 400, first and second housing portions 32, 42 are rotated relative to each other such that HME ports 432 of second housing portion 42 communicate with HME inlets 410 of first housing portion 32. In such a position, the MDI ports 434 of second housing portion 42 open against a solid section of disk shaped base portion 406 of first housing portion 32. In such a position, arm 416 covers area 246 and uncovers area 248 such that it is clear that the HME passage 34 is in use.

For the MDI position where fluid flows through the cylindrical MDI passage 38 of apparatus 400, first and second housing portions 32, 42 are rotated relative to each other such that MDI ports 434 of second housing portion 42 communicate with MDI inlets 408 of first housing portion 32. In such a position, the HME ports 432 of second housing portion 42 open against a solid section of cylindrical longitudinally extending portion 404 of first housing portion 32. In such a position, arm 416 covers area 248 and uncovers area 246 such that it is clear that the MDI passage 38 is in use.

In operation, the apparatus 400 is placed between the ventilator wye connection 24 and the tracheal tube 26 (or endotracheal tube). In the HME position, inspiratory and expiratory fluid flows back and forth through the HME medium 36, providing previously exhaled heat and moisture back to the patient. To use the apparatus 400 to deliver aerosolized medication via the MDI canister 28, the first and second housing portions 32, 42 are rotated relative to each other on a longitudinally extending axis for about ninety degrees so as to direct fluid flow into the interior cylinder 38 or MDI passage 38 instead of the HME medium 36. Then the MDI canister 28 is attached to the MDI nozzle or port 40 in the wall of the apparatus 400 and is discharged, with the discharge action being timed with the beginning of the inspiratory breath delivered by the ventilator. When the prescribed number of MDI discharges is complete, the MDI canister 28 is removed from the nozzle 40, and the housing portions 32, 42 are rotated relative to each other, now directing fluid flow again through the HME passage 34, with arm 418 automatically covering area 246 and sealing off MDI port 40 as the portions 32, 42 are rotated relative to each other back to the normal or HME position.

Apparatus 600 Specifically

As shown in FIG. 16, apparatus 600 generally includes the first interior section 34 (or HME portion or passage 34), the second interior section 38 (or MDI portion or passage 38), the housing 30 having the main or first housing portion 32 and the valve or second housing portion 42, the inlet 44 for receiving fluid from the mechanical ventilator 18, and the outlet 46 for directing fluid to a ventilated patient.

Apparatus 600 further includes a valve 602 for directing fluid to the first (HME) interior section 34 or the second (MDI) interior section 38, and a valve control or arm 604 extending from the valve 602 and having a distal portion 606 that closes off seat portion 62. An MDI or MDI canister 28 is shown in phantom in FIG. 16.

Valve housing portion 42 includes inlet 44. Inlet 44 can engage, such as via a male/female connection, a portion of a mechanical ventilator circuit. Inlet 44 is one-piece and integral with valve housing portion 42.

Valve housing portion 42 further includes valve seat portions 608, 610, 612. Valve seat portions 608, 610, 612 can have cylindrical seating faces to seat valve 602 where valve 602 is drum-shaped. Valve seat portions 608, 610, 612 can have spherical seating faces to seat valve 602 where valve 602 is ball or spherically shaped. Valve seat portions 608, 610, 612 are one-piece and integral with valve housing portion 42.

Valve housing portion 42 further includes outwardly tapering wall portions 614, 616 extending from respective valve seat portions 608, 610. Each of wall portions 614, 616 includes a respective bifurcated distal end 618, 620 (or portions 618, 620 of an endless annular bifurcated lip) for being engaged to an annular endless edge of main housing portion 32. In the case where valve 602 is a ball valve, wall portions 614, 616 may be part of a frustoconical section. Where valve 602 is a ball valve, reference numerals 622, 624 indicate further portions of such frustoconical section. Where valve 602 is a drum-shaped valve (such as shown in FIG. 18), portions 614, 616, 622, 624 can be shaped to smoothly lead into edges of housing portion 32, which can be formed in the shape of a cylinder or flattened cylinder or some other shape. Valve seat portion 612 can extend integrally from portions 622, 624 and can further extend to housing portions that laterally oppose portions 622, 624.

Valve housing portion 42 can have one or more openings for a structural connection between valve control arm 604 and valve 602. The one or more openings can be coaxial with an axis for valve 602. Such structural connection between valve control arm 604 and valve 602 can include a laterally extending axis.

Valve housing portion 42 includes an MDI port 626 leading into second (MDI) interior section 38 and an HME port 628 leading into first (HME) interior section 34. MDI port 626 confronts valve seat portion 612. HME port 628 also confronts valve seat portion 612.

One end of main housing portion 32 is engaged by valve housing portion 42. A second end of main housing portion 32 includes outlet 46. Main housing portion 32 includes the endless sidewall 56.

Endless sidewall 56 is preferably cylindrical in shape. Endless sidewall 68 is integral and one-piece with tapering housing portion 100. Where sidewall 68 is cylindrical, tapering housing portion 100 can be part of one spherical portion leading into outlet 46. Outlet 46 is one-piece and integral with portion 100 and with endless sidewall 56.

Main housing portion 32 further includes the divider 102 extending integrally between laterally opposing portions of sidewall 56. Divider 102 divides first (HME) interior section 34 from second (MDI) interior section 38. Divider 102 is generally planar. Divider 102 (in apparatus 10, 200, 400, 600, 800 and 900) can be curved or arcuate such that the MDI section can be tubular in shape, a configuration that may allow a greater volume for the HME section, thereby holding more HME medium to increase the performance of the HME section. At a first end, divider 102 is integral with an end wall or end wall portion 630. End wall or end wall portion 630 extends integrally between laterally opposing portions of sidewall 56 and engages and provides support for housing portion 612, which is a seat for valve 602. An HME inlet port 632 for first (HME) interior section 34 is formed in main housing portion 32 and confronts end wall or end wall portion 630 and sidewall 56. An MDI inlet port 634 for second (MDI) interior section 38 is formed in main housing portion 32 and confronts end wall or end wall portion 630 and sidewall 56. HME inlet port 632 communicates with HME port 628 of valve housing portion 42 and MDI inlet port 634 communicates with MDI port 626 of valve housing portion 42.

At a second end, divider 102 terminates short of outlet 46 to provide relatively large exit ports 636, 638 out of respective first and second interior sections 34, 38. It should be noted that divider 102, in any of the embodiments 10, 200, 400, 600, 800 and 900, may pivot or slide or change position so as to open up the HME or MDI section that is being used at the time. Such a change of position may be actuated by the valve control arm of the respective embodiment or by the rotating valve or housing portion or by some other structure.

First (HME) interior section 34 is bounded by divider 102, sidewall 56, tapering portion 100, end wall or end wall portion 630. First (HME) interior section 34 includes HME media 36. Media 36 provides heat and moisture exchange. Media 36 extends completely between divider 102 and sidewall 56 such that any fluid passing through first (HME) interior section 34 must pass through media 36 for pick-up (absorption) and/or dispersing of heat and moisture. Media 36 can include metallic layers spaced apart by a fibrous element. Media 36 can include superabsorbent polymer fibers. Bacterial/viral filters can be placed at one or more ends of media 36. For example, one filter can confront HME inlet port 632 and/or MDI inlet port 634. And/or one filter can confront HME exit port 636.

Second (MDI) interior section 38 is bounded by divider 102, sidewall 56, tapering portion 100, end wall or end wall portion 630. Second (MDI) interior section 38 generally is an empty chamber, except for conduit portion 64 of MDI port 40 that extends into MDI passage 38. Arm 604 and first housing portion 32 can be fixed relative to each other via a detent mechanism 640 having the ball snap 158 and ball receiver 160 as shown with apparatus 10.

MDI seat 62 is fixidly engaged on an exterior of sidewall 56 so as to confront MDI passage 38. If desired, MDI seat 62 can be integral with sidewall 56. If desired, MDI seat 62 can be a disk like depression in sidewall 56. If desired, MDI seat 62 can be integral and one-piece with tube or conduit portion 64. Opening or outlet 74 is oriented in a downstream direction to spray the drug or therapeutic agent downstream. If desired, tube portion 64 can include one or more openings to spray the therapeutic agent downstream and/or upstream and/or laterally and/or obliquely and/or toward divider 102 and/or toward sidewall 56.

First (HME) interior section 34 is immediately lateral of second (MDI) interior section 38 to minimize the longitudinal size (length) and lateral size (width) of apparatus 600. Such an arrangement minimizes the size of apparatus 600 as a whole. First (HME) interior section 34 is longitudinally extending and is relatively elongate to provide for pick-up and dissipation of heat and moisture over a relatively great area and to reduce the lateral size (width) of the apparatus 600. Second (MDI) interior section 38 is longitudinally extending and is relatively elongate to provide a chamber of a relatively great size for the formation of a plume or cloud of therapeutic agent 642 and to minimize the lateral size (width) of the apparatus 600.

Valve 602 is seated on the faces or seats of valve seat portions 608, 610, 612. Valve 602 can be a drum-shaped valve or a ball valve having the shape of a sphere. Valve 602 includes an HME wall 644 for blocking off HME ports 628 and 632 and an MDI wall 646 for blocking off MDI ports 626, 634. HME wall 644 extends between valve seat portions 610 and 612. MDI wall 646 extends between valve seat portions 608 and 612. Valve 602 includes a passage 648 having an inlet 650 and an outlet 652. Outlet 652 can be oriented to channel fluid to either the HME passage 34 or the MDI passage 38.

Valve 602 is operated or controlled with arm 604. Disposed between valve 602 and arm 604 is a shaft or axle 654. When MDI wall 646 blocks off ports 626, 634, fluid from the mechanical ventilator is forced into first (HME) interior section 34 via ports 628, 632. In such a position, the distal end portion 606 of arm 604 necessarily confronts MDI seat 62 and closes off the central opening 66 therein such that the stem 70 cannot be placed into the seat 62. In such a position, arm 604 can be locked to sidewall 56 via detent mechanism 640. When the arm 604 is in such a position, such position is a signal to the respiratory therapist that valve 602 is directing the fluid from the mechanical ventilator through the first (HME) interior section 34.

When wall 644 is blocking off HME ports 628, 632, arm 604 is swung away from receptor seat 62 to an out-of-the-way position indicated in phantom in FIG. 16. This out-of-the-way position signals to the respiratory therapist that valve 602 is directing fluid from the mechanical ventilator to and through the second (MDI) interior section 38 and that it is safe to spray the therapeutic agent from canister 28 into MDI interior section or passage 38.

In operation, a portion of circuit 12 is opened (such as at wye connection 24), and the apparatus 600 is placed therein via connections at the inlet 44 and outlet 46. When first engaged, valve 602 is open relative to the first (HME) interior section 34 and closed relative to the second (MDI) interior section 38 because such is the normal position of valve 602. When the ventilated patient requires a dose of the therapeutic agent 642, arm 604 is pivoted or swung to the out-of-the-way position such that valve wall 644 blocks off ports 628, 632 and such that valve wall 646 slides or pivots to confront valve seat portion 608 to open MDI ports 626, 634. In other words, arm 604 is swung to swing exit port 652 from being in communication with ports 628, 632 to being in communication with ports 626, 634. At all times, inlet port 650 of valve 602 is in communication with inlet 44 of second housing portion 42 such that at all times inlet 44 of second housing portion 42 is in communication with outlet 46 of first housing portion 32. When arm 604 is swung to the out-of-the-way position and the second (MDI) interior section 38 is open relative to valve 602, the MDI or MDI canister 28 is brought into engagement with MDI port 40. The MDI 28 is then operated to open the metering valve in the canister 28 to send a metered dose of therapeutic agent 642 out of opening or outlet 74 and into MDI passage 38. The plume or cloud of therapeutic agent 642 is then conveyed, via the fluid from the mechanical ventilator, out of MDI passage 38, through exit port 638, and into and through outlet 46 to the lungs of the patient being ventilated. Then the MDI 28 is withdrawn from the receptor 62 and the distal end portion 606 of arm 604 is snapped back to the housing portion 32, thereby closing valve 602 relative to the second (MDI) interior section 38 and opening valve 602 relative to the first (HME) interior section 34.

It should be noted that when patient fluid or gas is exhaled, it flows through whichever section 34 or 38 is open at the inlet 44.

It should be noted that a first safety feature is the distal end portion 606 of arm 604 closing off the seat portion 62 when valve 602 is open relative to the first (HME) interior section 34. A second safety feature is the out-of-the-way position of arm 604, which is a visual indicator to the operator or practitioner that valve 602 is closed relative to the first (HME) interior section 34 and open relative to the second (MDI) interior section 38.

It should be noted that it may be desirable to deposit a dose of therapeutic agent 642 into MDI passage 38, permit a cloud or plume of therapeutic agent to form without fluid being conveyed through the second (MDI) interior section or passage 38, and then open up the second (MDI) interior section 38 to fluid flow. In such a case, the length of arm 604 may be shortened and arm 604 may terminate short of receptor seat 62. In such a case, the second safety feature (the arm 604 being in the out-of-the-way position, i.e., in the swung outward and away position) still exists to warn the respiratory therapist that the second (MDI) interior section 38 is open relative to valve 602.

It should be noted that the apparatus 600 may be turned around 180 degrees such that fluid being conveyed from the mechanical ventilator enters outlet 46 and exits inlet 44 and such that valve 602 is positioned where fluid exits apparatus 600.

It should be noted that apparatus 600 may include a pair of valves 602, with one valve 602 confronting the inlet 44 and with one valve 602 confronting the outlet 46. The valves 602 can be tied together by exterior parallelogram pivoting bars or some other structure such that first (HME) interior section 34 is cut off at all times and at both ends from second (MDI) interior section 38. Such a structure may also be placed in embodiments 10, 200, 400, 800 and 900.

It should be noted that apparatus 600 can have separate outlets 46, one for the first (HME) interior section 34 and one for the second (MDI) interior section 38, where such outlets then communicate as in a wye.

It should be noted that, as with apparatus 200 and 400, an exterior portion or area of first housing portion 32 of apparatus 600, about MDI port 40, can be colored with a warning color such as red, to warn the practitioner that the MDI section 38 is active. Such an area is covered completely by arm 604 when arm 604 confronts the MDI port 40. Such an area is uncovered completely by arm 604 when the arm 604 is out-of-the-way of the MDI port 40. Such an area can also include the indicia "MDI ACTIVE."

Apparatus 800 Specifically

Apparatus 800 is shown in a side view in FIG. 18. Apparatus 800 includes all of the features of apparatus 600 except, whereas apparatus 600 includes a ball valve 602, apparatus 800 includes a drum shaped valve. The drum shaped valve directs fluid to the first (HME) interior section or the second (MDI) interior section. A valve control or arm 604 extends from the drum shaped valve via valve drive or valve axle 654. Apparatus 800 includes the housing 30 having the main or first housing portion 32 and the valve or second housing portion 42, the inlet 44 for receiving fluid from the mechanical ventilator 18, and the outlet 46 for directing fluid to a ventilated patient. The discussion as to embodiment 600 is hereby incorporated by reference into this portion of this document.

Apparatus 900 Specifically

Embodiment 900 includes the inlet 42, the outlet 46, the housing 30, the HME section 34, the MDI section 38, a lever or arm, a valve engaged to the lever or arm, and the general structure and shape as the other embodiments 10, 200, 400, 600 and 800. The lever or arm of embodiment 900 is designated as reference numeral 902. Embodiment 900 does not completely isolate the MDI and HME sections 38, 34 from each other as the other embodiments are capable of doing when the valves in such other embodiments are completely turned one way. The MDI section 38 is disposed generally centrally, parallel and lateral to the HME section 34, with HME material 36 surrounding the diameter of the MDI section 38. The MDI nozzle or port 40 is placed generally in a medial portion of the MDI section 38, and continues to the exterior of the housing 30. In other words, the proximal end of the nozzle or port 40 is on the exterior of the housing 30 and the distal end of nozzle or port 40 is disposed generally on an axis of the housing 30, between the inlet 42 and outlet 46 at a location somewhat closer to the inlet 42 than the outlet 46, and within the MDI section 38. The exterior housing 30 of the apparatus 900 may contain a depression or sunken well extending into the HME section 34. This depression or sunken well may be shaped to receive the MDI canister 28, which when in the depression or sunken well is closer to the MDI section 38 so as to shorten the nozzle and the distance that medication travels. The outlet 46 is typically open to both the MDI and HME sections 38, 34 as are the other embodiments. The MDI section 38 includes its own inlet 904 and outlet 906. The inlet 904 is substantially closed to fluid flow (or minimizes fluid flow) by a circular vane or butterfly valve 908 which rotates inside the MDI section 38 and is connected by a rotating strut or axis 910 which continues to the exterior of the apparatus and is engaged to the exterior arm or lever 902. When the lever 902 is raised such as shown in FIG. 19A, the vane or butterfly valve 908 rotates, opening the MDI section 38 to fluid flow. The vane 908 does not close the HME section 34 to fluid flow in this position as the valves in the other embodiments are capable of doing when such other valves are completely turned one way. Rather, fluid flow, meeting the slight resistance offered by the HME material 36, flows largely through the MDI section 38 and out through the outlet 46.

When the lever 902 is snapped into the closed position, the MDI section 38 is closed to fluid flow at the inlet 904, and the fluid flows around the MDI section 38, through the HME material 36, and out the outlet 46.

It should be noted that the MDI section 38 is housed in an internal tube or cylinder 912, as shown in FIG. 20A. Tube 912 is engaged within housing 30 via at least one longitudinal extension 914 that extends to and between tube 912 and housing 30. Longitudinal extension 914 may be paired with another extension positioned diametrically opposite of extension 914 and hidden behind nozzle 40 in FIG. 20A.

It should be noted that the HME media 36 is disposed annularly about tube 912 and between the exterior of tube 912 and the interior of the housing 30.

It should be noted that valve 908, when closed, confronts and substantially seals the inlet 904 of tube 912.

It should be noted that embodiment 900 may include the exterior graphics of "MDI ACTIVE" as shown in relation to embodiment 10 in FIGS. 2A and 2B.

Other Features of Apparatus 10, 200, 400, 600, 800 and 900

It should be noted that apparatus 10, 200, 400, 600, 800 or 900 as a whole or some portion thereof, such as first housing portion 32, or second housing portion 42, or some section or sections of portions 32, 42, can be transparent or translucent. For example, it may be desirable to see the plume or cloud of therapeutic agent 642 form and/or it may be desirable to see the position of the inlets and ports therein to note whether fluid is being directed to the first (HME) interior section 34 or the second (MDI) interior section 38.

In apparatus 10, 600, 800 and 900, first and second housing portions 32 and 42 can be welded together so as to be unitary and one-piece. Such an engagement maximizes a clean interior. Such an engagement minimizes tampering with the interior of housing 30.

When apparatus 10, 200, 600, 800 or 900 is placed in mechanical ventilating circuit 12, it should be noted that the MDI portion 38 may be disposed above the HME portion 34, or that the MDI portion 38 may be disposed below the HME portion 34, or that the MDI portion 38 may be disposed in a horizontal side to side relationship with the HME portion 34, or that the MDI portion 38 may be disposed in an oblique side to side relationship with the HME portion 34. It should be noted that the conventional MDI canister cannot be operated in an inverted position; however, it is conceivable that improved MDI canisters may be operable in any position.

"Medicated inhaler" means herein an MDI, a DPI, a nebulizer or other apparatus that can deliver via a gas a particulate medicine or drug that can be taken up by the bronchi (the final branching of the respiratory tract).

"MDI" means metered dose inhaler and means a pressured container or canister having a metering valve and drug therein. "MDI" further includes in its group a "DPI" or dry powder inhaler. "MDI" is not restricted to an aerosolized medication or drug delivered by an aerosol. "MDI" does not include the attendant mouthpiece or spacer or other equipment that receives the plume or cloud of medication that is dispensed by the metering valve of the "MDI."

"Humidifying apparatus" or "humidifying and heat exchange media" means an active or passive heat and moisture exchanger. Passive heat and moisture exchangers are preferred by the present invention.

An active heat and moisture exchanger is a heat and moisture exchanger that utilizes an external power source, such as a battery or alternating current provided by a power grid, to warm humidifying media or to perform another function. An active heat and moisture exchanger can include a microprocessor. An active heat and moisture exchanger includes heated humidifiers (HHs). Active heat and moisture exchangers include pass-over humidifiers, wick humidifiers, and bubble humidifiers.

A "passive heat and moisture exchanger" means an artificial nose or a heat and moisture exchanger that relies solely on the patient to warm and humidify (and optionally filter) inspired gases. Passive heat and moisture exchangers include HMEs, HMEFs, HHMEs, and HHMEFs, and HCHs.

"HME" means a passive heat and moisture exchanger. The group of "HMEs" includes HMEFs, HHMEs, and HHMEFs, HCHs, and other artificial noses.

A boosted "HME" means a passive heat and moisture exchanger that confronts, such as slightly downstream in the direction of a patient, a small heated (such as by electricity) element for warming the fluid, where the heated element may be covered by a textile having openings sufficiently large to permit passage of water molecules in the gaseous state, where such openings are sufficiently small to block passage of water molecules in a liquid state. One such textile is a Gortex® textile which is a federally registered mark owned by W.L. Gore and Associates of Newark, Del., where such textiles breathe and at the same time keep rainwater out.

As to the MDI portion 38 of the present HME/MDI apparatus and further as to the apparatus 10, 200, 400, 600, 800 and 900 as a whole, the following U.S. Patent or Patent Application Publications are hereby incorporated by reference in their entireties: 1) the Thiel U.S. Pat. No. 4,819,834 issued Apr. 11, 1989 and entitled Apparatus and Methods For Delivering A Predetermined Amount Of A Pressurized Fluid; 2) the Evans et al. U.S. Pat. No. 5,261,538 issued Nov. 16, 1993 and entitled Aerosol Testing Method; 3) the Jinks et al. U.S. Pat. No. 5,477,992 issued Dec. 26, 1995 and entitled Metered-Dose Aerosol Valves; 4) the Conroy et al. U.S. Pat. No. 5,938,085 issued Aug. 17, 1999 and entitled Valves For Dispensers; 5) the Abrams et al. U.S. Pat. No. 6,026,809 issued Feb. 22, 2000 and entitled Inhalation Device; 6) the Nilsson U.S. Pat. No. 6,089,227 issued Jul. 18, 2000 and entitled Device For An Inhaler; 7) the Sexton et al. U.S. Pat. No. 6,626,171 B2 issued Sep. 30, 2003 and entitled Powder/Liquid Metering Valve; and 8) the Castro et al. U.S. Pat. No. 6,640,805 B2 issued Nov. 4, 2003 and entitled Metering Valve For A Metered Dose Inhaler Having Improved Flow.

As to the HME portion 34 of the present HME/MDI apparatus and further as to the apparatus 10, 200, 400, 600, 800 and 900 as a whole, the following U.S. Patent or Patent Application Publications are hereby incorporated by reference in their entireties: 1) The Kuypers et al. U.S. Pat. No.

5,577,494 issued Nov. 26, 1996 and entitled Superabsorbent Fiber Compositions. Demonstrating Efficient Retention Of Exhaled Heat And Moisture; 2) the Rosenkoetter U.S. Pat. No. 5,590,644 issued Jan. 7, 1997 and entitled Heat and Moisture Exchanger For Breathing; 3) the Turnball U.S. Pat. No. 5,647,344 issued Jul. 15, 1997 and entitled Heat And Moisture Exchangers; 4) the Ryder U.S. Pat. No. 6,550,476 B1 issued Apr. 22, 2003 and entitled Heat-Moisture Exchanger And Nebulization Device; 5) the Diehl U.S. Pat. No. 6,588,421 B1 issued Jul. 8, 2003 and entitled HME Bypass System; and 6) the Marler et al. U.S. Patent Application Publication No. US 2004/0123974 A1 published Jul. 1, 2004 and entitled Heat And Moisture Filter Exchanger And Method. As indicated above, a great variety of heat and moisture exchanging media, or referred to interchangeably as HME medium, exists and the present invention is not limited to a certain kind or certain type of HME medium.

As to the present HME/MDI apparatus 10, 200, 400, 600, 800 and 900 as a whole and as to humidification in artificial airways, the following article is hereby incorporated by reference in its entirety to the extent permissible: the Richard D. Branson article entitled "Humidification for Patients with Artificial Airways," Respiratory Care, June 1999, Volume 44, Number 6, pages 630-642, published by Daedalus Enterprises Inc. in Irving, Tex.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalents of the claims are intended to be embraced therein.

I claim:

1. An HME/MDI apparatus for being placed in a circuit of a mechanical ventilator, comprising:
   a) a housing that comprises:
      i) an inlet having laterally opposing sections, with the inlet being adapted for engagement with the circuit of the mechanical ventilator;
      ii) an outlet having laterally opposing sections, with the outlet being adapted for engagement with the circuit of the mechanical ventilator, with the outlet being in fluid communication with the inlet;
      iii) a sidewall having laterally opposing sidewall portions, with a length between the laterally opposing sidewall portions being greater than a length between the laterally opposing sections of the inlet and being greater than a length between the laterally opposing sections of the outlet;
      iv) a first interior section between the inlet and outlet and being in fluid communication with the inlet and outlet, with the first interior section further being between said laterally opposing sidewall portions; and
      v) a second interior section between the inlet and outlet and being in fluid communication with the inlet and outlet, with the second interior section further being between said laterally opposing sidewall portions;
   b) an HME medium in the first interior section in the housing;
   c) an MDI port on the housing and being adapted for receiving an MDI, with the MDI port being in fluid communication with the second interior section of the housing such that medication from the MDI can be conveyed into the second interior section of the housing; and
   d) wherein the housing further comprises an arm and a valve, with the valve being operable to minimize fluid flow into at least one of the first and second interior sections, with said fluid flowing from the inlet to the outlet, with the arm being engaged to the valve such that movement of the arm moves the valve, with the arm having an arm portion confronting the MDI port, with said arm portion having a first position that renders the MDI port inoperable, with said arm portion having a second position that permits operation of the MDI port, with said first and second positions defining a position of said valve.

2. The HME/MDI apparatus of claim 1, wherein at least a portion of the first interior section is lateral of at least a portion of the second interior section.

3. The HME/MDI apparatus of claim 1, wherein at least a portion of the first interior section is immediately lateral of at least a portion of the second interior section.

4. The HME/MDI apparatus of claim 1, wherein the first interior section is disposed in parallel with the second interior section.

5. The HME/MDI apparatus of claim 1, with at least a portion of the arm being disposed outside of the housing such that positions of the arm can communicate to a caregiver open and closed positions of the valve in the housing relative to said at least one of the first and second interior sections.

6. The HME/MDI apparatus of claim 1, wherein the valve confronts one of the inlet and outlet.

7. The HME/MDI apparatus of claim 1, wherein the housing comprises a first housing portion and a second housing portion, with the first and second housing portions being rotatable relative to each other, with at least one of the first and second housing portions comprising a valve portion that is operated when the first and second housing portions are rotated relative to each other, with the valve portion being operable to minimize fluid flow into one of the first and second interior sections when said fluid flows from the inlet to the outlet.

8. The HME/MDI apparatus of claim 1, and further comprising a nebulizer, with the nebulizer being in fluid communication with the inlet of the housing, with the nebulizer discharging medication into the inlet, through the second interior section, and out of the outlet.

9. An HME/MDI apparatus for being placed in a circuit of a mechanical ventilator, comprising:
   a) a housing comprising an inlet, an outlet, an HME section, and an MDI section, with the HME section and MDI section being disposed in parallel in the housing;
   b) HME media in the HME section;
   c) an MDI port on the housing and leading to the MDI section;
   d) a valve in the housing, with the valve being operable to minimize fluid flow to at least one of the HME and MDI sections; and
   e) an arm comprising an arm portion disposed outside of and confrontable with the housing, with the arm being engaged to the valve such that movement of the arm portion moves the valve, with said arm portion having a first position that renders the MDI port inoperable, with said arm portion having a second position that permits operation of the MDI port, with said first and second positions defining respective positions of said valve.

10. The HME/MDI apparatus of claim 9, wherein said arm portion confronts the MDI port in the first position, and wherein said arm portion is out-of-the-way of the MDI port in the second position.

11. The HME/MDI apparatus of claim 10, and further comprising a warning on an exterior of the housing about the MDI port such that, when the arm portion is out-of-the-way of the MDI port, said warning is exposed to alert a caregiver that valve position is directing fluid through the MDI section of the housing.

12. The HME/MDI apparatus of claim 9, with the housing having longitudinal and lateral directions, with the longitudinal direction being defined by a flow of fluid from the inlet to the outlet, with the lateral direction being defined as traverse to the longitudinal direction, and with the valve turning on a lateral axis.

13. The HME/MDI apparatus of claim 9, with the housing having longitudinal and lateral directions, with the longitudinal direction being defined by a flow of fluid from the inlet to the outlet, with the lateral direction being defined as traverse to the longitudinal direction, and with the valve turning on a longitudinal axis.

14. The HME/MDI apparatus of claim 9, wherein the valve is open at all times relative to the inlet and outlet such that, regardless of a position of the valve and regardless of a position of the arm, fluid flow can be had at all times from the inlet to the outlet and from the outlet to the inlet such that fluid flow to a patient is never cut off.

15. An HME/MDI apparatus for being placed in a circuit of a mechanical ventilator, comprising:
   a) a housing comprising an inlet, an outlet, an HME section, and an MDI section;
   b) HME media in the HME section;
   c) an MDI port on the housing and leading to the MDI section;
   d) a valve in the housing, with the valve being operable to minimize fluid flow to at least one of the HME and MDI sections when said fluid flows from the inlet to the outlet;
   e) wherein the valve is open at all times relative to the inlet and outlet such that, regardless of a position of the valve, fluid flow can be had at all times from the inlet to the outlet and from the outlet to the inlet such that fluid flow to a patient is never cut off; and
   f) an arm engaged to the valve, with at least a portion of the arm disposed outside of the housing, with the arm controlling an opening and closing of the valve relative to at least one of the HME and MDI sections, with the arm including a portion confronting the MDI port when the valve is in one of the open and closed positions, with the MDI port being confronted by said portion of the arm when the valve is closed relative to the MDI section, and with said portion of the arm being out-of-the-way of the MDI port when the valve is open relative to the MDI section.

16. An HME/MDI apparatus for being placed in a circuit of a mechanical ventilator, comprising:
   a) a housing comprising an inlet, an outlet, an HME section, and an MDI section;
   b) HME media in the HME section;
   c) an MDI port on the housing and leading to the MDI section;
   d) a valve in the housing, with the valve being operable to minimize fluid flow into at least one of the HME and MDI sections when said fluid flows from the inlet to the outlet; and
   e) an arm engaged to the valve, with at least a portion of the arm disposed outside of the housing, with the arm controlling an opening and closing of the valve relative to at least one of the HME and MDI sections, with the arm including a portion confronting the MDI port when the valve is in one of the open and closed positions, with the MDI port being confronted by said portion of the arm when the valve is closed relative to the MDI section, and with said portion of arm being out-of-the-way of the MDI port when the valve is open relative to the MDI section.

17. The HME/MDI apparatus of claim 16, wherein the HME section is disposed in parallel to the MDI section in the housing.

* * * * *